US006458561B1

(12) United States Patent
Bandman et al.

(10) Patent No.: US 6,458,561 B1
(45) Date of Patent: Oct. 1, 2002

(54) HUMAN NIM1 KINASE

(75) Inventors: Olga Bandman, Mountain View, CA (US); Angela Molteni, Cantù (IT); Paola Magnaghi, Milan (IT); Roberta Bosotti, Nerviano (IT); Emanuela Scacheri; Antonella Isacchi, both of Milan (IT); David M. Hodgson, Palo Alto, CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/523,849

(22) Filed: Mar. 13, 2000

(51) Int. Cl.$^7$ .............................. C12P 2/06; C12P 21/04; C12N 15/00; C12N 15/09; C12N 15/63; C12N 15/74; C12N 5/00; C12N 5/02; C07H 21/02; C07H 21/04

(52) U.S. Cl. .................. 435/69.1; 435/70.1; 435/320.1; 435/325; 536/23.1; 536/23.5; 536/24.1

(58) Field of Search ............................... 536/23.5, 23.1, 536/24.1; 435/69.1, 320.1, 325

(56) References Cited

U.S. PATENT DOCUMENTS 5,795,740 A * 8/1998 Platica et al.

FOREIGN PATENT DOCUMENTS

WO    WO 00/73469    7/2000    ........... C12N/15/54

OTHER PUBLICATIONS

Accession No. X97630, Database GenEmbl, Espinosa, L., Cytogent. Cell Gent. 81(3–4): 278–282, 1998.*
Accession No. Z83869, Database GenEmbl, Drewes, G. et al., cell 89(2): 297–308, 1997.*
Accession No. AI335850, Database GenBank EST, NCI–C-GAP, Feb. 13, 1999.*
Accession No. R59486 (GenBank EST, Hillier et al, May 24, 1995.*
Sambrook et al, Molecular Cloning, Cold Spring Harbor Laboratory Press, 1989, pp. 16.3–16.4, 16.17–16.22, 16.28, 16.29, 17–37–17.41.*
NCI/NINDS–CGAP, GenBank Accession No. AI609751 (GI:4618918), May 12, 1999.
Hardie and Hanks (1995) *The Protein Kinase Facts Books*, vol. I, Academic Press, San Diego CA, pp. 7–20.
Bairoch, A. et al., "The Prosite database, its status in 1995", *Nucleic Acids Res.* 24: 189–196 (1996).
Isselbacher et al., *Harrison's Principles of Internal Medicine*, McGraw–Hill, New York, N.Y., pp. 416–431, 1887 (1994).
Haribabu, B. et al., "Human calcium–calmodulin dependent protein kinase I: cDNA cloning, domain structure and activation by phosphorylation at threonine–177 by calcium–calmodulin dependent protein kinase I kinase", *EMBO J.* 14: 3679–3686 (1995).

Dyck, J.R.B. et al., "Regulation of 5'–AMP–activated Protein Kinase Activity by the Noncatalytic β and γ Subunits", *J. Biol. Chem.* 271(30): 17798–17803 (1996).
Egan, S.E. and Weinberg, R.A., "The pathway to signal achievement", *Nature* 365: 781–783 (1993).
Li, B. et al., "prk, a Cytokine–inducible Human Protein Serine/Threonine Kinase Whose Expression Appears to be Down–regulated in Lung Carcinomas", *J. Biol. Chem.* 271(32): 19402–19408 (1996).
Brenner, S.E. et al., "Assessing sequence comparison methods with reliable structurally identified distant evolutionary relationships", *Proc. Natl. Acad. Sci. USA* 95: 6073–6078 (May 1998).
Spiess, A. and Ivell, R., "Normalization of RNA Hybridization Signals by Means of SYBR® Green II–Stained 28S or 18S Ribosomal RNA and a Phosphor Imager", *Biotechniques* 26: 46–50 (Jan. 1999).
Guo, S. and Kemphues, K.J., (Direct Submission) NCBI Accession No. U22183 (GI 733122), Apr. 18, 1996.
Wilson, R. et al., (Direct Submission), GenBank Sequence Database (Accession CAB04433), National Center for Biotechnology Information, National Library of Medicine, Bethesda, Maryland, 20894 (GI 3877329), Sep. 6, 1999.
Drewes, G. (Direct Submission), GenBank Sequence Database (Accession CAB06294), National Center for Biotechnology Information, National Library of Medicine, Bethesda, Maryland, 20894 (GI 2052189), Apr. 25, 1997.
Peng, C.Y. et al., (Direct Submission), GenBank Sequence Database (Accession AAC15093), National Center for Biotechnology Information, National Library of Medicine, Bethesda, Maryland, 20894 (GI 3089349), Apr. 28, 1998.
Wang, Z., (Direct Submission), GenBank Sequence Database (Accession BAA82673), National Center for Biotechnology Information, National Library of Medicine, Bethesda, Maryland, 20894 (GI 5672676), Aug. 6, 1999.
Taboada, E.N. and Hickey, D.A., (Direct Submission), GenBank Sequence Database (Accession AAB81837), National Center for Biotechnology Information, National Library of Medicine, Bethesda, Maryland, 20894 (GI 2564680), Oct. 26, 1997.
Espinosa, L. and Navarro, E., (Direct Submission) NCBI Accession No. CAA66229 (GI 1749794), Oct. 1, 1998.

* cited by examiner

*Primary Examiner*—Geetha P. Bansal
*Assistant Examiner*—Natalie Davis
(74) *Attorney, Agent, or Firm*—Incyte Genomics, Inc.; Lynn E. Murry

(57) ABSTRACT

The invention provides a nucleic acid molecule which encodes the human NIM1 kinase. It also provides for the use of the nucleic acid molecule, fragments, variants and complements thereof and of the protein, portions thereof and antibodies thereto for characterization, diagnosis, evaluation, treatment, or prevention of disorders associated with expression. The invention additionally provides expression vectors and host cells for the production of the protein and a transgenic organism or model system.

12 Claims, 12 Drawing Sheets

```
                10          19   28         37   46         55
5' AGA GAT GAG ATC CCG CAG GGA CGT GGG GGC CTC CCA GGG GCA TTT ACG CAC 64          73   82         91   100        109
CAG AGT GCA AGA TTC TCT GGC CAT CAA GGG AAA TAG CAA ACA GAA GCC TTT GTC 118         127  136        145  154        163
CTG GGG CAC AGC CAC CCA CAA AGC ATC AGA CTC CAC GTC TGG CCA GAA AGT 172         181  190        199  208        217
TCC TGG AGT CCC ATC AGG CCA GTG GGT ATG TAA CAT GTG CCT AAT TGT ACA GCT 226         235  244        253  262        271
AGA GCC TGC AAG TTC AAC GTG AGG GAA GGT GGG AAA TGT CTT GAG TGA GGC GAG 280         289  298        307  316        325
CAG CTC CTG GCT GGG CTG GGC AGA CTC AGC TAC CAC GTT CAC TGC CTT CCT CTC 334         343  352        361  370        379
ACT AAA GCC GAG AGG GAG GCT GCT CAG CTC TCA GGA AAA CTC TTT TGA ACC CTG 388         397  406        415  424        433
GGC ACC TGC TGT CCT CAG TTG GCA TCT CCC ACC CTC TGA GCC TCT TCT GCT CCT

```
442                 451                 460                 469                 478                 487
GCA CAA CCT         TCT CTG AGA         TGG AGA CGT         GAG CCC CCG         TGG ACG ATG         ACT
 A   Q   P           S   L   R           W   R   R           E   P   P           W   T   M           T 496                 505                 514                 523                 532                 541
GCA GTG TAT         ATG AAT GGA         GGT GGC CTG         GTG AAC CAC         TAT GCC CGG         TGG GAT
 A   V   Y           M   N   G           G   G   L           V   N   H           Y   A   R           W   D 550                 559                 568                 577                 586                 595
CGC GAC AGT         GAA AGT GGC         TGT CAG ACC         GAG AGT AGC         AAG GTG CGG         TGG GAG
 R   D   S           E   S   G           C   Q   T           E   S   S           K   V   R           W   E 604                 613                 622                 631                 640                 649
CAG CAG CCC         CGC CAG CTG         ACG CCC TTC         GAG AAA CTG         ACA CAG GAC         ATG TCC
 Q   Q   P           R   Q   L           T   P   F           E   K   L           T   Q   D           M   S 658                 667                 676                 685                 694                 703
GAG AAG GTG         AGG GAG ATC         ACG CTG GGG         AAA CGG ATA         GGC TTC TAC
 E   K   V           R   E   I           T   L   G           K   R   I           G   F   Y 712                 721                 730                 739                 748                 757
CGA ATT GGA         GAA ATC GGA         AGT GGA AAC         TTC TCC CAA         GTG AAG CTT         GGG ATT
 R   I   G           E   I   G           S   G   N           F   S   Q           V   K   L           G   I
```

```
        766      775      784      793      802      811
CAC TCC CTA ACC AAA GAA AAG GTG GCC ATT AAG ATC CTG GAC AAG ACC AAG TTA
 H   S   L   T   K   E   K   V   A   I   K   I   L   D   K   T   K   L 820      829      838      847      856      865
GAC CAG AAA ACC CAG AGG CTA CTA TCC CGA GAA ATC TCC AGC ATG GAA AAG CTG
 D   Q   K   T   Q   R   L   L   S   R   E   I   S   S   M   E   K   L 874      883      892      901      910      919
CAC CAT CCC AAC ATC CGC CTT TAC GAA GTG GAG ACC CTA TCC AAG CTG
 H   H   P   N   I   R   L   Y   E   V   E   T   L   S   K   L 928      937      946      955      964      973
CAC TTG GTG ATG GAG TAT GCA GGG GGT GAG CTC TTC GGA AAA ATT AGC ACT
 H   L   V   M   E   Y   A   G   G   E   L   F   G   K   I   S   T 982      991      1000     1009     1018     1027
GAG GGG AAG CTC TCT GAA CCA GAA AGC AAG CTC ATC TTC TCC CAG ATT GTG TCT
 E   G   K   L   S   E   P   E   S   K   L   I   F   S   Q   I   V   S 1036     1045     1054     1063     1072     1081
GCC GTG AAG CAC ATG GAG CAT CAT GAA AAC CAA ATT ATT CAT AGA GAT CTG AAA GCA GAA
 A   V   K   H   M   E   H   H   E   N   Q   I   I   H   R   D   L   K   A   E

FIGURE 1C
```

```
      1090            1099            1108            1117            1126            1135
AAT GTA TTC TAT ACC AGT AAT ACT TGT GTG AAG GTG GGC GAT TTT GGA TTC AGC
 N   V   F   Y   T   S   N   T   C   V   K   V   G   D   F   G   F   S 1144            1153            1162            1171            1180            1189
ACA GTA AGC AAA AAA GGT GAA ATG CTG AAC ACT TTC TGT GGG TCT CCT CCC TAC
 T   V   S   K   K   G   E   M   L   N   T   F   C   G   S   P   P   Y 1198            1207            1216            1225            1234            1243
GCT GCG CCT GAA CTC TTC CGG GAC GAG CAC TAC ATC GGC ATT TAC GTG GAT ATC
 A   A   P   E   L   F   R   D   E   H   Y   I   G   I   Y   V   D   I 1252            1261            1270            1279            1288            1297
TGG GCC TTG GGG GTG CTT TTG TAC TTC ATG GTG ACT GGC ACC ATG CCA TTT CGG
 W   A   L   G   V   L   L   Y   F   M   V   T   G   T   M   P   F   R 1306            1315            1324            1333            1342            1351
GCA GAA ACC GTG GCC AAA CTA AAA AAG AGC ATC CTC GAG GGC ACA TAC AGT GTA
 A   E   T   V   A   K   L   K   K   S   I   L   E   G   T   Y   S   V 1360            1369            1378            1387            1396            1405
CCG CCG CAC GTG TCA GAG CCC TGC CAC CGA CTC ATC CGA GGA GTC CTT CAG CAG
 P   P   H   V   S   E   P   C   H   R   L   I   R   G   V   L   Q   Q
```

FIGURE 1D

```
                              1414                1423                1432                1441                1450                1459
                              ATC CCC ACG GAG AGG TAC GGA ATC GAC TGC ATC ATG AAT GAT GAA TGG ATG CAA
                               I   P   T   E   R   Y   G   I   D   C   I   M   N   D   E   W   M   Q 1468                1477                1486                1495                1504                1513
                              GGG GTG CCA TAC CCT ACA CCT TTG GAA CCT TTC CAA CTG GAT CCC AAA CAT TTG
                               G   V   P   Y   P   T   P   L   E   P   F   Q   L   D   P   K   H   L 1522                1531                1540                1549                1558                1567
                              TCG GAA ACC AGC ACT CTC AAG GAA GAA GAA AAT GAG GTC AAA AGC ACT TTA GAA
                               S   E   T   S   T   L   K   E   E   E   N   E   V   K   S   T   L   E 1576                1585                1594                1603                1612                1621
                              CAT TTG GGC ATT ACA GAA GAG CAT ATT CGA AAT AAC CAA GGG AGA GAT GCT CGC
                               H   L   G   I   T   E   E   H   I   R   N   N   Q   G   R   D   A   R 1630                1639                1648                1657                1666                1675
                              AGC TCA ATC ACA GGG GTC TAT AGA ATT ATT TTA CAT AGA GTC CAA AGG AAG AAG
                               S   S   I   T   G   V   Y   R   I   I   L   H   R   V   Q   R   K   K 1684                1693                1702                1711                1720                1729
                              GCT TTG GAA AGT GTC CCA ATG CTA CCA GAC CCT AAA GAA AGA GAC CTC
                               A   L   E   S   V   P   M   L   P   D   P   K   E   R   D   L
```

FIGURE 1E

```
                                          1738                   1747                   1756                   1765                   1774                   1783
                               AAA AAA GGG TCC CGT GTC TAC AGA GGG ATA AGA CAC ACA TCC AAA TTT TGC TCG
                                K   K   G   S   R   V   Y   R   G   I   R   H   T   S   K   F   C   S 1792                   1801                   1810                   1819                   1828                   1837
                               ATT TTA TAA ATT GCA CTA GAC TGC TTG TAA CTA ACC AAG ATG ATT GTT GCT GCT
                                I   L 1846                   1855                   1864                   1873                   1882                   1891
                               TCT AAA TTT TTT TCA AGG ACA ACT TGA GTG GAG ACA TTT TTG TAA TTT TTA AAT 1900                   1909                   1918                   1927                   1936                   1945
                               AAA CTT AAA TTT GAG ATA TGC AAA AAA AAA AAG GGC GGC CGC CGA CTA 1954                   1963                   1972                   1981                   1990                   1999
                               GTG AGC TCG TCG ACC CGG GAA TTA ATT CCG GAC CGG TAC CTG CAG GCG TAC CAG 2008                   2017                   2026                   2035                   2044                   2053
                               CTT TCC CTA TAG TGG AGT CCG TAT TAA ACT TGG CCG TAA TCA TGG CAT AAC TTG

TTC CCT G 3'
```

FIGURE 1F

| Clone Human Tissue Category | Count | Absolute Found | Absolute Abundance |
|---|---|---|---|
| Cardiovascular System | 2472285 | 0/62 | 0 |
| Connective Tissue | 1205592 | 1/38 | 1 |
| Digestive System | 375714 | 0/111 | 0 |
| Embryonic Structures | 84970 | 0/16 | 0 |
| Endocrine System | 179593 | 0/43 | 0 |
| Exocrine Glands | 240308 | 0/59 | 0 |
| Genitalia, Female | 344493 | 0/82 | 0 |
| Genitalia, Male | 411465 | 1/103 | 1 |
| Germ Cells | 28289 | 0/4 | 0 |
| Hemic and Immune System | 643113 | 0/144 | 0 |
| Liver | 78332 | 0/20 | 0 |
| Musculoskeletal System | 135466 | 0/38 | 0 |
| Nervous System | 709414 | 10/144 | 10 |
| Pancreas | 93477 | 0/21 | 0 |
| Respiratory System | 335356 | 0/73 | 0 |
| Sense Organs | 19263 | 0/8 | 0 |
| Skin | 60390 | 0/13 | 0 |
| Stomatognathic System | 10993 | 0/4 | 0 |
| Unclassified/Mixed | 89773 | 0/3 | 0 |
| Urinary Tract | 237771 | 0/53 | 0 |
| Totals | 4442057 | 12/1039 | 12 |

HUMAN NIM1 KINASE

FIELD OF THE INVENTION

This invention relates to a nucleic acid molecule which encodes human NIM1 kinase and to the use of the nucleic acid molecule and the protein it encodes in the characterization, diagnosis, prevention, and treatment of brain disorders and cancers, particularly breast cancer.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the protein kinases of nematode, fly, rat, and man have common chemical and structural features and modulate the same general cellular activity. Comparisons of the nucleic acid and protein sequences from organisms where structure and/or function are known accelerate the investigation of human sequences and allow the development of model systems for testing diagnostic and therapeutic agents for human conditions, diseases, and disorders.

Protein kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controling activities of eukaryotic cells. It is estimated that more than 1000 of the 10,000 proteins active in a typical mammalian cell are phosphorylated. The high energy phosphate which drives activation is generally transferred from adenosine triphosphate (ATP) or guanosine triphosphate (GTP) to a particular protein by protein kinases and removed from that protein by protein phosphatases. Phosphorylation is roughly analogous to turning on a molecular switch, and it occurs in response to extracellular signals (mediated by such molecules as hormones, neurotransmitters, growth and differentiation factors), cell cycle checkpoints, and environmental or nutritional stresses. When the switch goes on, the appropriate protein kinase activates a metabolic enzyme, regulatory protein, receptor, cytoskeletal protein, ion channel or pump, or transcription factor.

The protein kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate both threonine and tyrosine residues.

Protein kinases may be categorized into families by the different amino acid residues (generally between 5 and 100 residues) located on either side of, or inserted into loops of, the catalytic domain. These residues allow the regulation of each kinase as it recognizes and interacts with its target protein. Almost all kinases contain a similar 250–300 amino acid catalytic domain with 11 subdomains distributed across two lobes. The N-terminal lobe, which contains subdomains I–IV, binds and orients the ATP donor molecule. The larger C terminal lobe, which contains subdomains VIA-XI, binds the protein substrate and carries out the transfer of the gamma phosphate from ATP to the hydroxyl group of a serine, threonine, or tyrosine residue. Subdomain V spans the N and C terminal lobes.

Each of the 11 subdomains contain specific residues and motifs or patterns of amino acids that are characteristic of that subdomain and are highly conserved (Hardie and Hanks (1995) *The Protein Kinase Facts Books*, Vol I, Academic Press, San Diego Calif., pp. 7–20). In particular, two protein kinase signature sequences have been identified in the kinase domain, the first containing an active site lysine residue involved in ATP binding, and the second containing an aspartate residue important for catalytic activity. If a protein is found to contain the two protein kinase signatures, the probability of that protein being a protein kinase is close to 100% (MOTIFS search program, Genetics Computer Group, Madison Wis.; Bairoch et al. (1996) Nucleic Acids Res 24:189–196).

STK Families

The second messenger dependent protein kinases primarily mediate the effects of second messengers such as cyclic AMP (cAMP), cyclic GMP, inositol triphosphate, phosphatidylinositol, 3,4,5-triphosphate, cyclic ADP ribose, arachidonic acid, diacylglycerol and calcium-calmodulin. The cyclic-AMP dependent protein kinases (PKA) are important members of the STK family. cAMP is an intracellular mediator of hormone action in all prokaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cAMP in most of these cells. Altered PKA expression is implicated in a variety of disorders and diseases including cancer, thyroid disorders, diabetes, atherosclerosis, and cardiovascular disease (Isselbacher et al. (1994) *Harrison's Principles of Internal Medicine*, McGraw-Hill, New York N.Y., pp. 416–431 and 1887).

Calcium-calmodulin (CaM) dependent protein kinases are also members of STK family. Calmodulin is a calcium receptor that mediates many calcium regulated processes by binding to target proteins in response to the binding of calcium. The principle target protein in these processes is CaM dependent protein kinases (CaMK). CaMK are involved in regulation of smooth muscle contraction, glycogen breakdown (phosphorylase kinase), and neurotransmission (CaMK I and CaMK II). CaMK I phosphorylates a variety of substrates including the neurotransmitter related proteins synapsin I and II, the gene transcription regulator, CREB, and the cystic fibrosis conductance regulator protein, CFTR (Haribabu et al. (1995) *EMBO J* 14:3679–86). CaMK II also phosphorylates synapsin at different sites and controls the synthesis of catecholamines in the brain through phosphorylation and activation of tyrosine hydroxylase. Many of the CAMK are activated by phosphorylation in addition to binding to CaM. CaMK may autophosphorylate or be phosphorylated by another kinase as part of a "kinase cascade".

Another ligand-activated protein kinase is 5'-AMP-activated protein kinase (AMPK; Dyck et al. (1996) J Biol Chem 271:17998–17803). Mammalian AMPK is a regulator of fatty acid and sterol synthesis through phosphorylation of the enzymes acetyl-CoA carboxylase and hydroxymethylglutaryl-CoA reductase and mediates responses of these pathways to cellular stresses such as heat shock and depletion of glucose and ATP. AMPK is a heterotrimeric complex comprised of a catalytic alpha subunit and two non-catalytic beta and gamma subunits that are believed to regulate the activity of the alpha subunit. Subunits of AMPK have a much wider distribution in non-lipogenic tissues such as brain, heart, spleen, and lung than expected: This distribution suggests that its role may extend beyond regulation of lipid metabolism alone.

The mitogen-activated protein kinases (MAPK) are also members of the STK family, and they regulate intracellular signaling pathways. MAPK mediate signal transduction from the cell surface to the nucleus via phosphorylation cascades. Several subgroups have been identified, and each manifests different substrate specificities and responds to distinct extracellular stimuli (Egan and Weinberg (1993) Nature 365:781–783). MAP kinase signaling pathways are present in mammalian cells as well as in yeast. The extracellular stimuli which activate mammalian pathways include epidermal growth factor, ultraviolet light, hyperosmolar medium, heat shock, endotoxic lipopolysaccharide, and pro-inflammatory cytokines such as tumor necrosis factor and interleukin-1. Altered MAPK expression is implicated in a variety of disease conditions including cancer, inflammation, immune disorders, and disorders affecting growth and development.

Proliferation-related kinase (PRK) is a serum/cytokine inducible STK that is involved in regulation of the cell cycle and cell proliferation in human megakaroytic cells (Li et al. (1996) J Biol Chem 271:19402–8). PRK is related to the polo family of STKs implicated in cell division. PRK is downregulated in lung tumor tissue and may be a proto-oncogene whose deregulated expression in normal tissue leads to oncogenic transformation.

The cyclin-dependent protein kinases (CDKs) are another group of STKs that control the progression of cells through the cell cycle. Cyclins are small regulatory proteins that act by binding to and activating CDKs which then trigger various phases of the cell cycle by phosphorylating and activating selected proteins involved in the mitotic process. CDKs are unique in that they require multiple inputs to become activated. In addition to the binding of cyclin, CDK activation requires the phosphorylation of a specific threonine residue and the dephosphorylation of a specific tyrosine residue.

The discovery of nucleic acid molecules encoding a human NIM1 kinase (hNIM) provides new compositions which are useful in the characterization, diagnosis, prevention, and treatment of brain disorders and cancers, particularly breast cancer.

SUMMARY OF THE INVENTION

The invention is based on the discovery of a substantially purified nucleic acid molecule encoding a human NIM1 kinase which satisfies a need in the art by providing compositions useful in the characterization, diagnosis, prevention, and treatment of brain disorders and cancers, particularly breast cancer.

The invention provides a substantially purified nucleic acid molecule which encodes the human NIM1 kinase comprising SEQ ID NO:2. The invention also provides a composition comprising SEQ ID NO:1 or a fragment or a complement thereof. The invention further provides a mammalian variant of the nucleic acid molecule selected from SEQ ID NOs:24–30. The invention still further provides a fragment of at least 18 consecutive nucleotides selected from about nucleotide 414 to about 1414 of SEQ ID NO:1, SEQ ID NOs:3–30, or the complements thereof. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for detecting a nucleic acid molecule in a sample, the method comprising the steps of hybridizing a probe or complementary nucleic acid molecule to at least one nucleic acid in a sample, forming a hybridization complex; and detecting the hybridization complex, wherein the presence of the hybridization complex indicates the presence of the nucleic acid molecule in the sample. In one aspect, the method further comprises amplifying the nucleic acids of the sample prior to hybridization. The nucleic acid molecule or a fragment or a complement thereof may comprise an element on an array.

The invention also provides a method for using a nucleic acid molecule or a fragment or a complement thereof to screen a library of molecules or compounds to identify at least one ligand which specifically binds the nucleic acid molecule, the method comprising combining the nucleic acid molecule with a library of molecules or compounds under conditions allowing specific binding, and detecting specific binding to the nucleic acid molecule, thereby identifying a ligand which specifically binds the nucleic acid molecule. In one aspect, the libraries of molecules and compounds include DNA and RNA molecules, peptides, PNAs, proteins, and the like.

The invention further provides an expression vector containing at least a fragment of the nucleic acid molecule which is contained within a host cell. The invention still further provides a method for producing a protein, the method comprising the steps of culturing the host cell under conditions for the expression of the protein and recovering the protein from the host cell culture.

The invention provides an isolated and purified protein comprising SEQ ID NO:2 or a portion thereof. Additionally, the invention provides a pharmaceutical composition comprising a substantially purified protein or a portion thereof in conjunction with a pharmaceutical carrier.

The invention provides a method for using at least a portion of the protein to produce antibodies. The invention also provides a method for using a protein to screen a library of molecules or compounds to identify at least one ligand which specifically binds the protein, the method comprising combining the protein with the library of molecules or compounds under conditions allowing specific binding, and detecting bound protein, thereby identifying a ligand which specifically binds the protein. Such libraries of molecules and compounds include agonists, antagonists, antibodies, DNA and RNA molecules, immunoglobulins, drug compounds, mimetics, peptides, pharmaceutical agents, and other ligands. The invention further provides an analogous method which uses the protein to purify a ligand. The method involves combining the protein with a sample under conditions to allow specific binding, recovering the bound protein, and separating the protein from the ligand to obtain purified ligand.

The invention additionally provides antibodies identified by screening methods using or antibodies produced against the human NIM1 kinase. A method of preparing an antibody comprising immunizing an animal with the human NIM1 kinase or an antigenically-effective portion thereof under conditions to elicit an antibody response; isolating animal antibodies; and screening the isolated antibodies with NIM1 kinase thereby identifying an antibody specifically binds Nim1 kinase. In one aspect these antibodies are useful as diagnostic compositions in identification of brain disorders and cancers. In another aspect, the antibody may be administered as a pharmaceutical composition to treat brain disorders and cancers associated with the overexpression of human NIM1 kinase.

The further provides a method for inserting a marker gene into the genomic DNA of a mammal to disrupt the expression of the natural nucleic acid. The invention also provides a method for using a nucleic acid molecule to produce a mammalian model system, the method comprising constructing a vector containing the nucleic acid molecule selected from SEQ ID NOs:1 and 3–30; transforming the vector into an embryonic stem cell; selecting a transformed embryonic stem; microinjecting the transformed embryonic stem cell into a mammalian blastocyst, thereby forming a chimeric blastocyst; transferring the chimeric blastocyst into a pseudopregnant dam, wherein the dam gives birth to a chimeric offspring containing the nucleic acid molecule in its germ line; and breeding the chimeric mammal to produce a homozygous, mammalian model system.

BRIEF DESCRIPTION OF THE FIGURES AND TABLE

FIGS. 1A, 1B, 1C, 1D, 1E, and 1F show the nucleic acid molecule (SEQ ID NO:1) encoding the human NIM1 kinase (SEQ ID NO:2). The alignment was produced using MACD-NASIS PRO software (Hitachi Software Engineering, South San Francisco Calif.).

FIG. 2 shows electronic northern analysis of the highly specific expression of human NIM1 kinase in brain tissue (74%) and cancers of the breast (connective tissue) and prostate (genitalia, male). The electronic northern was produced using the LIFESEQ Gold database (Incyte Pharmaceuticals, Palo Alto Calif.).

FIGS. 4A, 4B, and 4C demonstrate the conserved chemical and structural similarities among the catalytic domains of human NIM1 kinase (3317608CD1; SEQ ID NO:2), Caenorhabditis elegans STK (g3877329; SEQ ID NO:31), Rattus norvegicus STK (g2052189; SEQ ID NO:32), human C-TAK1 (g3089349; SEQ ID NO:33), Rattus norvegicus salt-inducible kinase(g5672676; SEQ ID NO:34), Drosophila melanogaster K78 protein kinase (g2564680; SEQ ID NO:35), and human EMK1(g1749794; SEQ ID NO:36). The alignment was produced using the MEGALIGN program of LASERGENE software (DNASTAR, Madison Wis.).

Figure 5:
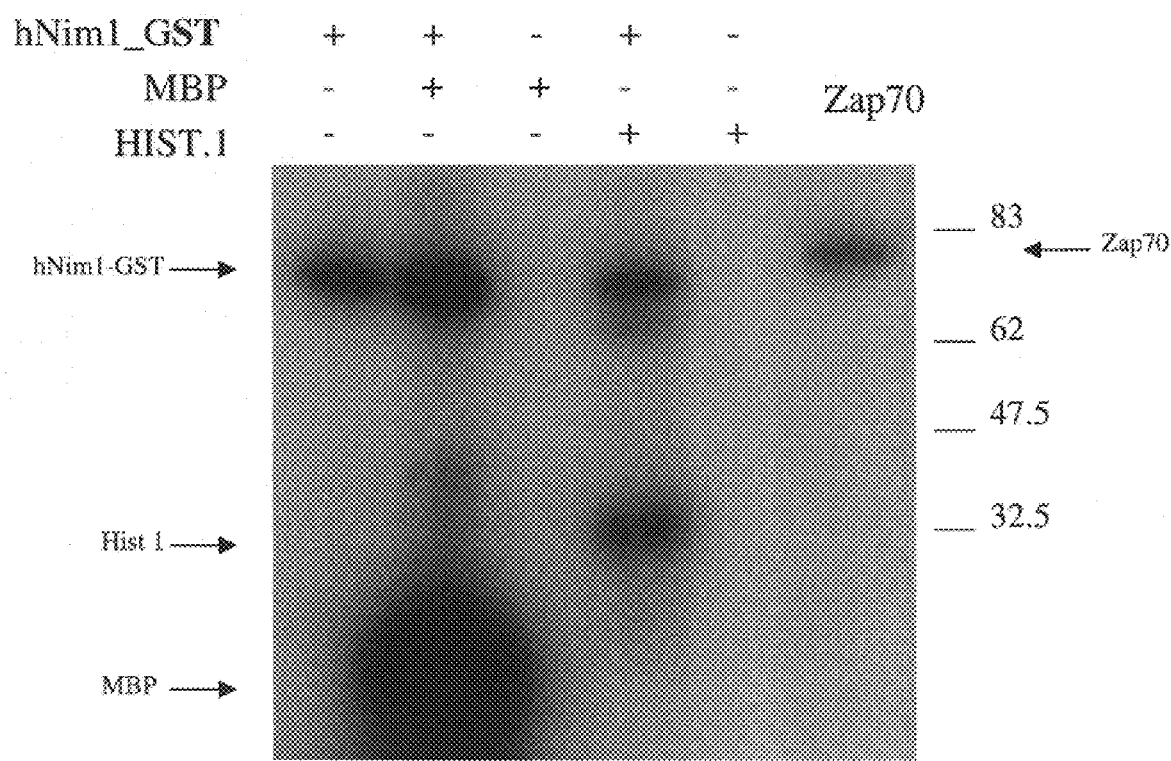

FIG. 5 shows the human NIM1 (hNIM1) kinase assay. The enzyme, hNIM1-GST; substrates: myelin basic protein (MBP) and histone (HIST.1); and the positive control, ZAP70 (70 kd zeta-chain (TCR) associated protein kinase). The designations + and – indicate the presence or absence of the human NIM kinase and substrates in the lane. Size markers in kilodaltons are shown along the right side of the gel.

DESCRIPTION OF THE INVENTION

It is understood that this invention is not limited to the particular machines, materials and methods described. It is also to be understood that the terminology used herein is for the purpose of describing particular embodiments only and is not intended to limit the scope of the present invention which will be limited only by the appended claims. As used herein, the singular formis "a," "an," and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"NIM1 kinase" refers to a substantially purified enzyme obtained from any mammalian species, including bovine, ovine, porcine, rodent, canine, simian, and preferably the human species, and from any source, whether natural, synthetic, semi-synthetic, or recombinant.

"Biologically active" refers to a protein having structural, immunological, regulatory, or chemical functions of a naturally occurring, recombinant or synthetic molecule "Complementary" refer to the natural hydrogen bonding by base pairing between purines and pyrimidines. For example, the sequence A-C-G-T forms hydrogen bonds with its complements T-G-C-A or U-G-C-A. Two single-stranded molecules may be considered partially complementary, if only some of the nucleotides bond, or completely complementary, if nearly all of the nucleotides bond. The degree of complementarity between nucleic acid strands affects the efficiency and strength of the hybridization and amplification reactions.

"Derivative" refers to the chemical modification of a nucleic acid molecule or amino acid sequence. Chemical modifications can include replacement of hydrogen by an alkyl, acyl, or amino group or glycosylation, pegylation, or any similar process which retains or enhances biological activity or lifespan of the molecule or sequence.

"Fragment" refers to an Incyte clone or any part of a nucleic acid molecule which retains a usable, functional characteristic. Useful fragments are generally at least 18 consecutive nucleotides in length and include oligonucleotides which may be used in hybridization, amplification or screening technologies or in regulation of replication, transcription or translation.

"Hybridization complex" refers to a complex between two nucleic acid molecules by virtue of the formation of hydrogen bonds between purines and pyrimidines.

"Ligand" refers to any molecule, agent, or compound which will bind specifically to a complementary site on a nucleic acid molecule or protein. Such ligands stabilize or modulate the activity of nucleic acid molecules or proteins of the invention and may be composed of at least one of the following: inorganic and organic substances including nucleic acids, proteins, carbohydrates, fats, and lipids.

"Nucleic acid molecule" refers to a nucleic acid sequence, oligonucleotide, nucleotide, polynucleotide, DNA molecule, or any fragment or complement thereof. It may be DNA or RNA of genomic or synthetic origin, double-stranded or single-stranded, and combined with carbohydrate, lipids, protein or other materials to perform a particular activity such as transformation or form a useful composition such as a peptide nucleic acid (PNA). It may contain untranslated 5' or 3' regulatory regions or introns. Preferably, the nucleic acid molecule has from about 15 to 10,000 nucleotides, more preferably from about 60 to 6,000 nucleotides and most preferably about 400 to 5000 nucleotides. "Oligonucleotide" is substantially equivalent to the terms amplimer, primer, oligomer, element, target, and probe, is preferably single stranded, and preferably is about 15 to 60 nucleotides in length and more preferably, about 22 to 25 nucleotides.

"Protein" refers to an amino acid sequence, oligopeptide, peptide, polypeptide or portions thereof whether naturally occurring or synthetic.

"Portion" refers to any part of a protein used for any purpose, but especially for the screening of a library of molecules or compounds to identify molecules which specifically bind to that portion of the protein or for the production of antibodies.

"Reporter molecules" are chemical or biochemical moieties used for labeling a polynucleotide, a polypeptide, or an antibody. They include, but are not limited to, radionuclides, enzymes, substrates, cofactors, inhibitors, fluorescent agents, chromogenic agents, chemiluminescent agents, magnetic particles, and the like. Reporter molecules specifically bind, establish the presence of, and allow quantification of a particular polynucleotide, polypeptide, or antibody.

"Sample" is used herein in its broadest sense. A sample containing polynucleotides, polypeptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA in solution or bound to a substrate; a cell; a tissue; a tissue print; a fingerprint, skin or hair; and the like.

"Similarity" as applied to polynucleotide sequences, refers to the quantified residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

"Specific binding" or "specifically binding" refers to the interaction between two molecules. In the case of a polynucleotide, specific binding may involve hydrogen bonding between sense and antisense strands or between one stand and a protein which affects its replication or transcription, intercalation of a molecule or compound into the major or minor groove of the DNA molecule, or interaction with at least one molecule which functions as a transcription factor, enhancer, repressor, and the like. In the case of a polypeptide, specific binding may involve interactions with polynucleotides, as described above or with molecules or compounds such as agonists, antibodies, antagonists, and the like. Specific binding is dependent upon the presence of structural features that allow appropriate chemical or molecular interactions between molecules.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

THE INVENTION

The invention is based on the discovery of a nucleic acid molecule which encodes human NIM1 kinase and on the use of the nucleic acid molecule, or fragments thereof, and protein, or portions thereof, directly or as compositions in the characterization, diagnosis, treatment, or prevention of brain disorders and cancers.

The nucleic acid molecule encoding NIM1 kinase of the present invention was first identified as a kinase by Block II homology match between Incyte Clone 670279 from the cerebellum library (CRBLNOT01) and a putative STK of *C. elegans* (g733122) important for the polarity of zygote division and differentiation. The full length nucleic acid molecule, Incyte Clone 3317608 (SEQ ID NO:1) was sequenced and assembled from the Incyte LIFESEQ GOLD database (Mar 99 release) template 200700.1, the assembly 670279CB1 and Incyte Clones (Library): 3317608H 1 (PROSBPT03),4313713H1 (BRAFNOT01), 4617082H1 (BRAYDIT01), 4711644H1 (BRAIHCT01), 2286324H1 (BRAINON01), 2286816H1 (BRAINON01), 2287217H1 (BRAINON01), 2286816R6 (BRAINON01), 2286816T6 (BRAINON01), 3317608T6 (PROSBPT03), 4201896T6 (BRAITUT29), 462481 T6 (FIBRTXT02), 6559834H1 (BRAFNON02), 670279F1 (CRBLNOT01), 670279H1 (CRBLNOT01), 670279R1 (CRBLNOT01), 670279R6 (CRBLNOT01), 670279T6 (CRBLNOT01), and 4936446H1 (BRAXNOT03) and which are SEQ ID NOs:3–23, respectively. Useful fragments of the polynucleotide that encodes SEQ ID NO:2 include a fragment of at least 18 consecutive nucleotides selected from about nucleotide 414 to about nucleotide 1414 of SEQ ID NO:1, SEQ ID NOs:3–23 or the complements thereof.

FIGS. 1A–F show the sequence of the nucleic acid molecule and its deduced translation into amino acids. Incyte Clone number 3317608 which contains the coding region for the human NIM1 kinase has been deposited in the American Type Culture Collection (ATCC; Manassas Va.) and has the Patent Deposit Designation: PT-1217.

As shown in FIG. 2, electronic northern analysis showed highly differential expression of the transcript encoding NIM1 kinase in the nervous system. All of these libraries were from brain; five were associated with cancer, three, with stroke, two, with Huntington's disease and one, with epilepsy. The transcript was found to be expressed only two other times in the LIFESEQ database (Incyte Pharmaceuticals) which contains 1039 libraries and over 5 million sequences, in cancerous breast fibroblasts, FIBRTXT02, and in cancerous prostate, PROSBPT03.

Figure 3:
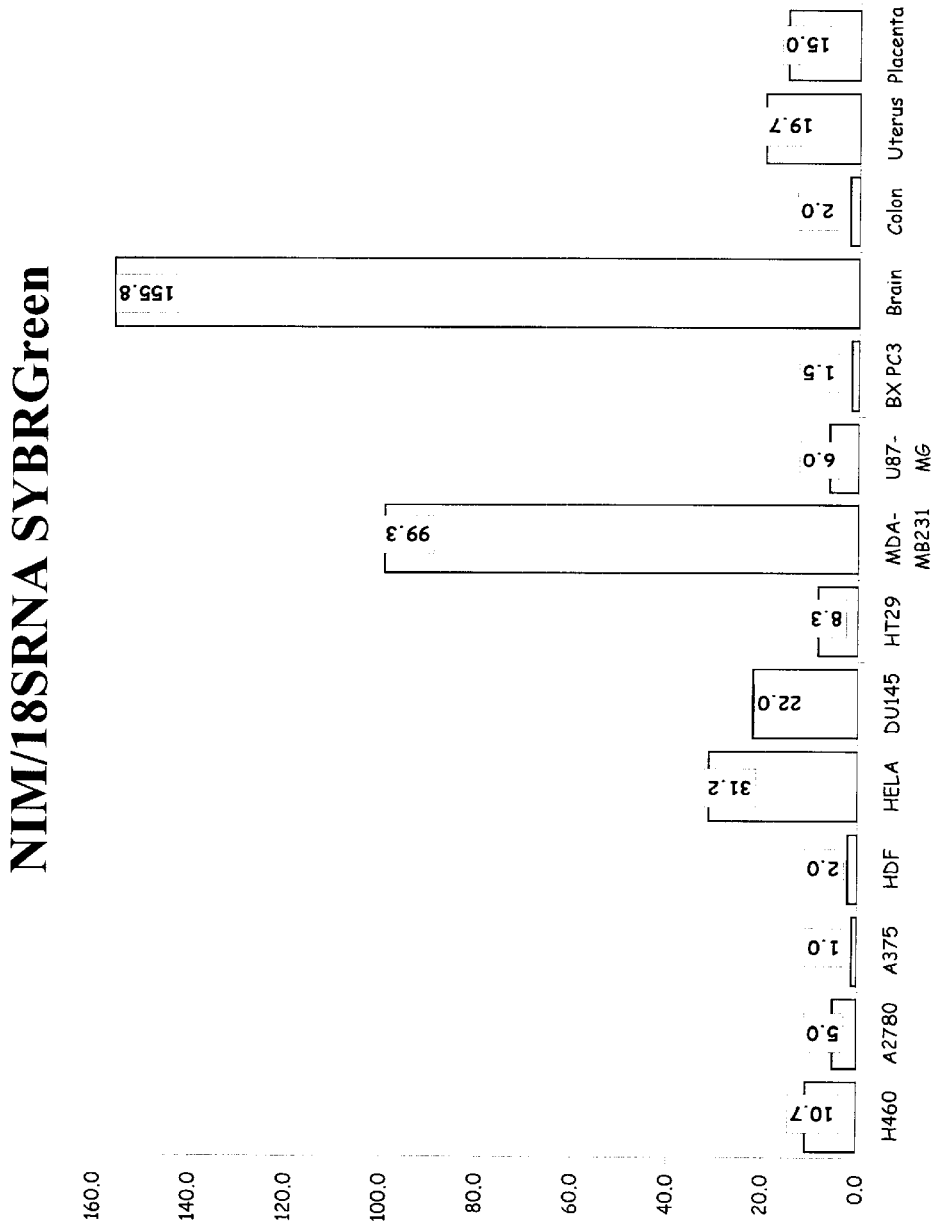
FIG. 3 shows a graph of transcript expression produced using quantitative PCR in various cell lines and tissues. The x axis shows fold expression; and the y axis, the cell lines (H460, A2780, A375, HDF, HELA, DU145, MDA-MB231, U87-MG and BX-PC3) and tissues (brain, colon, uterus and placenta tissues).

As presented in FIG. 3, northern analysis was also performed in the laboratory using quantitative PCR. Expression of human NIM1 kinase transcripts is shown in H460, A2780, A375, HDF, HELA, DU145, MDA-MB231, U87-MG and BX-PC3 cell lines and in brain, colon, uterus and placenta tissues. Of particular note, human breast carcinoma cell line, MDA-MB231, and brain tissue show approximately 100 and 155 fold expression of NIM1 kinase transcripts respectively. Greater than 5-fold expression was also see in cell lines representing carcinomas of the brain, cervix, colon, lung, ovary, and prostate and in normal uterus and placenta.

NIM1 kinase comprising the amino acid sequence of SEQ ID NO:2 is 436 amino acids in length and has a potential signal sequence from M1 to A18, potential phosphorylation sites at residues S56, T108, T114, S123, S169, S221, S282, Y288, T311, T332, T349, S359, S420, and T429. The human NIM1 kinase, as shown in FIG. 4, is used as the reference for numbering the conserved residues, motifs, and subdomains of catalytic region of the kinases (SEQ ID NOs:2 and 31–36) in the alignment. The residues, motifs and subdomains are: subdomain 1 extends from G81 to V88; subdomain 2, has conserved residues A101 and K103; subdomain 3 has the invariant F121; subdomain 5 extends from E151 to E 157 and shares the invariant residues M150 and Y152; subdomain 6B which represents the catalytic loop, extends from H194 to N201; subdomain 7, has the highly conserved triplet, D214, F215, and G216; subdomain 8, extends from T229 to F242 and contains the A238, P239, E240 motif; subdomain 9 has the invariant D253, subdomain 11 has the invariant R244 which interacts with the APE motif of subdomain 8. The C terminal boundary of the catalytic domain begins with H248, A249 and F250. Both PFAM and PRINTS analyses confirm kinase domains. Useful fragments of the polypeptide of SEQ ID NO:2 include a fragment of at least 6 consecutive amino acids selected from about residue 1 to about residue 295 of SEQ ID NO:2.

FIG. 5 shows the human NIM1 kinase assay. hNIM1 kinase-GST autophosphorylated as shown in lanes 1, 2, and 4 and phosphorylated its substrates MBP, lane 2, and HIST.1, lane 4. In the absence of kinase, substrates MBP, lane 3, and HIST.1, lane 5, show no phosphorylation. Lane 6 shows the positive control ZAP70.

Mammalian variants of the nucleic acid molecules encoding the human NIM1 kinase were identified by using BLAST or BLAST2 ((Basic Local Alignment Search Tool: Altschul et al. (1997) Nucleic Acids Res 25:3389–3402; Altschul (1993) J Mol Evol 36:290–300; and Altschul et al. (1990) J Mol Biol 215:403–10, with default parameters), to identify clones in the LWFESEQ or ZOOSEQ databases (Incyte Pharmaceuticals) which aligned with SEQ ID NOs:1 and 3–23. The mammalian variants are ZOOSEQ database template (Dec 99 build) 216150.1 (SEQ ID NO:24) and Incyte clones: 701925441H1 (RALITXS03), 701910632H1 (RABYUNN02), 701905514H1 (RABYUNS09), 701293826H1 (RABXNOT04), and 700949543H1 (RASPNON02) from rat and 700706950H1 (MNBFNOT01) from monkey; SEQ ID NOs:25–30, respectively. These nucleic acid molecules are particularly useful for producing transgenic organisms which model human disorders and upon which potential therapeutic treatments for such disorders may be tested.

The nucleic acid molecule, SEQ ID NO:1, and fragments thereof (SEQ ID NOs:3–30) may be used in hybridization, amplification, and screening technologies to identify and distinguish among SEQ ID NO:1 and similar molecules in a sample. The human molecules and their mammalian variants may be used to produce transgenic organisms which model the human disorders and upon which potential therapeutic treatments may be tested. Toxicology studies, clinical trials, and subject/patient treatment profiles may be performed and monitored using the nucleic acid molecules, proteins, antibodies and molecules and compounds identified using the nucleic acid molecules and proteins of the present invention.

Characterization and Use of the Invention
cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. Three library preparations representative of the invention are described in the EXAMPLES below. The consensus sequences were chemically and/or electronically assembled from fragments including Incyte clones and extension and/or shotgun sequences using computer programs such as PHRAP (P Green, University of Washington, Seattle Wash.), GELVIEW Fragment Assembly system (Genetics Computer Group, Madison Wis.), and AUTOASSEMBLER application (PE Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the HYDRA microdispenser (Robbins Scientific, Sunnyvale Calif.), MICROLAB 2200 system (Hamilton, Reno Nev.), and the DNA ENGINE thermal cycler (PTC200; MJ Research, Watertown Mass.). Machines used for sequencing include the ABI PRISM 3700, 377 or 373 DNA sequencing systems (PE Biosystems), the MEGABACE 1000 DNA sequencing system (Amersham Pharmacia Biotech), and the like. The sequences may be analyzed using a variety of algorithms which are well known in the art and described in Ausubel et al. (1997; *Short Protocols in Molecular Biology*, John Wiley & Sons, New York N.Y., unit 7.7) and Meyers (1995; *Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the nucleic acid molecules of interest. Incomplete assembled sequences are inspected for identity using various algorithms or programs such as CONSED (Gordon (1998) Genome Res 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries may be used to extend the nucleic acid sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55C to about 68C. When extending a sequence to recover regulatory elements, it is preferable to use genomic, rather than cDNA libraries.

USE OF THE MAMMALIAN NUCLEIC ACID MOLECULES

Hybridization

The nucleic acid molecule and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the human NIM1 kinase, allelic variants, or related molecules. The probe may be DNA or RNA, may be single stranded and should have at least 50% sequence identity to any of the nucleic acid sequences, SEQ ID NOs:3–30. Hybridization probes may be produced using oligolabeling, nick translation, end-labeling, or PCR amplification in the presence of a reporter molecule. A vector containing the nucleic acid molecule or a fragment thereof may be used to produce an MRNA probe in vitro by addition of an RNA polymerase and labeled nucleotides. These procedures may be conducted using commercially available kits such as those provided by Amersham Pharmacia Biotech.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60° C., which permits the formation of a hybridization complex between nucleic acid sequences that contain some mismatches. Subsequent washes are performed at higher stringency with buffers such as 0.2×SSC with 0.1% SDS at either 45° C. (medium stringency) or 68° C. (high stringency). At high stringency, hybridization complexes will remain stable only where the nucleic acid molecules are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or Triton X-100 and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods known in the art. Oligonucleotides may be used as either probes or targets in an array. The array can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc. Natl. Acad. Sci. 93:10614–10619; Baldeschweiler et al. (1995) PCT application WO95/251116; Shalon et al. (1995) PCT application WO95/35505; Heller et al. (1997) Proc. Natl. Acad. Sci. 94:2150–2155; and Helleret al. (1997) U.S. Pat. No. 5,605,662.)

Hybridization probes are also useful in mapping the naturally occurring genomic sequence. The probes may be hybridized to: 1) a particular chromosome, 2) a specific region of a chromosome, or 3) artificial chromosome construction such as human artificial chromosome (HAC), yeast artificial chromosome (YAC), bacterial artificial chromosome (BAC), bacterial P1 construction, or single chromosome cDNA libraries.

Expression

A multitude of nucleic acid molecules encoding NIM1 kinase may be cloned into a vector and used to express the protein, or portions thereof, in host cells. The nucleic acid sequence can be engineered by such methods as DNA shuffling (U.S. Pat. No. 5,830,721) and site-directed mutagenesis t.e create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, nucleic acid molecule, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional pBLUESCRIPT vector (Stratagene, La Jolla Calif.) or pSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian nucleic acid molecule is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), calmodulin binding peptide (CBP), 6-His, FLAG, MYC, and the like. GST, CBP, and 6-His are purified using commercially available affinity matrices such as immobilized glutathione, calmodulin, and metal-chelate resins, respectively. FLAG and MYC are purified using commercially available monoclonal and polyclonal antibodies. A proteolytic cleavage site may be located between the desired protein sequence and the heterologous moiety for ease of separation following purification. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431 A peptide synthesizer (PE Biosystems). A protein or portion thereof may be substantially purified by preparative high performance liquid chromatography and its composition confirmed by amino acid analysis or by sequencing (Creighton (1984) *Proteins, Structures and Molecular Properties*, W H Freeman, New York N.Y.).

Preparation and Screening of Antibodies

Various hosts including goats, rabbits, rats, mice, humans, and others may be immunized by injection with human NIM1 kinase or any portion thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:31–42; Cote et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the human NIM1 kinase may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The human NIM1 kinase or a portion thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols*, Humana Press, Totowa N.J.).

Labeling of Molecules for Assay

A wide variety of labels and conjugation techniques are known by those skilled in the art and may be used in various nucleic acid, amino acid, and antibody assays. Synthesis of labeled molecules may be achieved using Promega (Madison Wis.) or Amersham Pharmacia Biotech kits for incorporation of a labeled nucleotide such as $^{32}$P-dCTP, Cy3-dCTP or Cy5-dCTP or amino acid such as $^{35}$S-methionine. Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

DIAGNOSTICS

The nucleic acid molecules, fragments, oligonucleotides, complementary RNA and DNA molecules, and PNAs and may be used to detect and quantify altered gene expression, absence/presence vs. excess, expression of mRNAs or to monitor mRNA levels during therapeutic intervention. Similarly antibodies which specifically bind the human NIM1 kinase may be used to quantitate the protein. Disorders associated with altered expression include akathesia, Alzheimer's disease, amnesia, amyotrophic lateral sclerosis, anxiety, hereditary ataxias, cerebral palsy, dementia, dermatomyositis, dystonias, Down's syndrome, epilepsy, ischemic cerebrovascular disease, cerebelloretinal hemangioblastomatosis, Huntington's disease, bacterial and viral meningitis, multiple sclerosis, muscular dystrophy, myasthenia gravis, cerebral neoplasms, neurofibromatosis, Parkinson's disease, Pick's disease, polymyositis, retinitis pigmentosa, schizophrenia, stroke, and cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The diagnostic assay may use hybridization or amplification technology to compare gene expression in a biological sample from a patient to standard samples in order to detect altered gene expression. Qualitative or quantitative methods for this comparison are well known in the art.

For example, the nucleic acid molecule or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If the amount of label in the patient sample is significantly altered in comparison to the standard value, then the presence of the associated condition, disease or disorder is indicated.

In order to provide a basis for the diagnosis of a condition, disease or disorder associated with gene expression, a normal or standard expression profile is established. This may be accomplished by combining a biological sample taken from normal subjects, either animal or human, with a probe under conditions for hybridization or amplification. Standard hybridization may be quantified by comparing the values obtained using normal subjects with values from an experiment in which a known amount of a substantially purified target sequence is used. Standard values obtained in this manner may be compared with values obtained from samples from patients who are symptomatic for a particular condition, disease, or disorder. Deviation from standard values toward those associated with a particular condition is used to diagnose that condition.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) Current Protocols in Immunology, Wiley-Interscience, New York N.Y.; and Pound, supra.)

THERAPEUTICS

Chemical and structural similarity, in the context of the kinase catalytic domain, exists between regions of human NIM1 kinase (SEQ ID NO:2) and the kinases shown in FIGS. 4A–4C (SEQ ID NOs: 31–35. In addition, gene expression is highly associated with brain, prostate, and breast and with cancers as shown in FIGS. 2 and 3. The human NIM1 kinase appears to play a role in disorders of the brain and nervous system, particularly brain cancer, stroke, epilepsy and Huntington's disease, and cancers of the brain, cervix, colon, lung, ovary, and prostate. In the treatment of conditions associated with highly increased expression such as brain and breast cancers, it is desirable to decrease expression or protein.activity.

In one embodiment, an inhibitor, antagonist or antibody of human NIM1 kinase may be administered to a subject to treat or prevent a condition associated with increased expression or activity. Examples of such conditions include, but are not limited to, akathesia, Alzheimer's disease, amnesia, amyotrophic lateral sclerosis, anxiety, hereditary ataxias, cerebral palsy, dementia, dermatomyositis, dystonias, Down's syndrome, epilepsy, ischemic cerebrovascular disease, cerebelloretinal hemangioblastomatosis, Huntington's disease, bacterial and viral meningitis, multiple sclerosis, muscular dystrophy, myasthenia gravis, cerebral neoplasms, neurofibromatosis, Parkinson's disease, Pick's disease, polymyositis, retinitis pigmentosa, schizophrenia, stroke, and cancers such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a pharmaceutical composition comprising an inhibitor, antagonist or antibody of NIM1 kinase in conjunction with a pharmaceutical carrier may be administered to a subject to treat or prevent a condition associated with altered expression or activity of the endogenous protein including, but not limited to, those provided above.

In an additional embodiment, a vector expressing the complement of the nucleic acid molecule or fragments thereof may be administered to a subject to treat or prevent a condition associated with altered lifespan, expression, or activity of the protein including, but not limited to, those described above.

Any of the nucleic acid molecules, complementary molecules and fragments thereof, proteins or portions thereof, vectors delivering these nucleic acid molecules or proteins, and their ligands may be administered in combination with other therapeutic agents. Selection of the agents for use in combination therapy may be made by one of ordinary skill in the art according to conventional pharmaceutical principles. A combination of therapeutic agents may act synergistically to effect prevention or treatment of a particular condition at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the gene encoding NIM1kinase. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library of nucleic acid molecules or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening and Purification Assays

The nucleic acid molecule encoding the human Nim1 kinase may be used to screen a library of molecules or compounds for specific binding affinity. The libraries may be aptamers, DNA molecules, RNA molecules, PNAs, peptides, proteins such as transcription factors, enhancers, repressors, and other ligands which regulate the activity, replication, transcription, or translation of the nucleic acid molecule in the biological system. The assay involves combining the nucleic acid molecule or a fragment thereof with the library of molecules under conditions allowing specific binding, and detecting specific binding to identify at least one molecule which specifically binds the single stranded or double stranded nucleic acid molecule.

In one embodiment, the polynucleotide of the invention may be incubated with a library of isolated and purified molecules or compounds and binding activity determined by methods well known in the art, e.g., a gel-retardation assay (U.S. Pat. No. 6,010,849) or a reticulocyte lysate transcriptional assay. In another embodiment, the polynucleotide may be incubated with nuclear extracts from biopsied and/or cultured cells and tissues. Specific binding between the polynucleotide and a molecule or compound in the nuclear extract is initially determined by gel shift assay and may be later confirmed by raising antibodies against that molecule or compound. When these antibodies are added into the assay, they cause a supershift in the gel-retardation assay.

In another embodiment, the polynucleotide may be used to purify a molecule or compound using affinity chromatography methods well known in the art. In one embodiment, the polynucleotide is chemically reacted with cyanogen bromide groups on a polymeric resin or gel. Then a sample is passed over and reacts with or binds to the polynucleotide. The molecule or compound which is bound to the polynucleotide may be released from the polynucleotide by increasing the salt concentration of the flow-through medium and collected.

In a further embodiment, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, human NIM1 kinase or a portion thereof may be used to screen libraries of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a polypeptide on their cell surface can be used in screening assays. The cells are screened against libraries or a plurality of ligands and the specificity of binding or formation of complexes between the expressed polypeptide and the ligand may be measured. Specific binding between the protein and molecule may be measured. Depending on the kind of library being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the polypeptide specifically compete with a test compound capable of binding to the polypeptide or oligopeptide or portion thereof. Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it may be expressed as the ratio, LD50/ED50. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. No. 5,175,383 and U.S. Pat. No. 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeniy are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

In additional embodiments, the nucleic acid molecules which encode the mammalian protein may be used in any molecular biology techniques that have yet to be developed, provided the new techniques rely on properties of nucleic acid molecules that are currently known, including, but not limited to, such properties as the triplet genetic code and specific base pair interactions.

EXAMPLES

It is to be understood that this invention is not limited to the particular machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, preparation of the human cerebellum (CRBLNOT01), prostate (PROSBPT03), and normalized brain (BRAINON01) libraries will be described.

I cDNA Library Construction

Cerebellum

The tissue used for cerebellum library construction was obtained from a 69 year-old, Caucasian male (RT95–05–0301; International Institute for Advanced Medicine, Exton Pa.). The frozen tissue was homogenized and lysed using a POLYTRON homogenizer (PT-3000; Brinkmann Instruments, Westbury N.J.). The reagents and extraction procedures were used as supplied in the RNA Isolation kit (Stratagene). The lysate was centrifuged over a 5.7 M CsCl cushion using an SW28 rotor in an L8–70M ultracentrifuge (Beckman Coulter, Fullerton Calif.) for 18 hr at 25,000 rpm at ambient temperature. The RNA was extracted twice with phenol chloroform, pH 8.0, and once with acid phenol, pH 4.0; precipitated using 0.3 M sodium acetate and 2.5 volumes of ethanol; resuspended in water; and treated with DNase for 15 min at 37C. The RNA was isolated with the OLIGOTEX kit (Qiagen, Chatsworth Calif.) and used to construct the cDNA library.

Prostate

Diseased prostate tissue removed from a 59-year-old Caucasian male during a radical prostatectomy was used to construct the PROSBPT03 library. Pathology for the tumor indicated adenocarcinoma, Gleason grade 3+3, with microscopic foci involving the right and left sides peripherally. The tumor was confined and did not involve the capsule. High-grade prostatic intraepithelial neoplasia was identified on the right side peripherally. The patient presented with elevated prostate specific antigen (PSA). Family history included cerebrovascular disease in both parents and prostate cancer in a sibling.

To construct the cDNA library, 2.4 micrograms of polyA RNA was used according to the recommended protocols in the SUPERSCRIPT Plasmid system (Life Technologies). First strand cDNA synthesis was accomplished using oligo d(T) priming, and second strand synthesis was performned using a combination of DNA polymerase I, *E. coli* ligase, and RNase H. The cDNA was blunted with T4 polymerase, and a Sal I linker was added to the blunt end of the cDNA. The Sal I adapted, double stranded cDNAs were the digested with Not I and fractionated on a SEPHAROSE CL4B column (Amersham Pharmacia Biotech).

Those cerebellum cDNAs exceeding 400 bp were ligated into pSPORT I plasmid which was subsequently transformed into DH5α competent cells (Life Technologies). Those prostate cDNAs exceeding 400 bp were ligated into the NotI and EcoRI sites of the pINCY plasmid (Incyte Pharmaceuticals) which was subsequently transformed into competent DH5α or ELECTROMAX DH10B competent cells (Life Technologies).

Normalized Brain

For purposes of example, the normalization of the human brain library (BRAINON01) is described. About $4.9 \times 10^6$ independent clones of the BRAINOT03 plasmid library in *E. coli* strain DH12S competent cells (Life Technologies) were grown in liquid culture under carbenicillin (25 mg/l) and methicillin (1 mg/ml) selection following transformation by electroporation. To reduce the number of excess cDNA copies according to their abundance levels in the library, the cDNA library was normalized in a single round according to the procedure of Soares et al. (1994, Proc Natl Acad Sci 91:9228–9232), with the following modifications. The primer to template ratio in the primer extension reaction was increased from 2:1 to 10:1. The dNTP concentration in the reaction was reduced to 150 μM for each dNTP to allow the generation of longer (400 to 1000 nt) primer extension products. The reannealing hybridization was extended from 13 to 48 hr. The single stranded DNA circles of the normalized library were purified by hydroxyapatite chromatography and converted to partially double-stranded by random priming, followed by electroporation into *E. coli* strain DH10B competent cells (Life Technologies).

II Construction of pINCY Plasmid

The plasmid was constructed by digesting the pSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, *E. coli* strain JM109.

An intermediate plasmid produced by the bacteria (pSPORT 1-ΔRI) showed no digestion with EcoRI and was digested with Hind III (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRi, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MINIPREP Kit (Edge Biosystems, Gaithersburg Md.) or the REAL Prep 96 plasmid kit (Qiagen). This kit consists of a 96-well block with reagents for 960 purifications. The recommended protocol was employed except for the following changes: 1) the bacteria were cultured in 1 ml of sterile Terrific Broth (Life Technologies) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4C.

The cDNAs were prepared for sequencing using the MICROLAB 2200 system (Hamilton, Reno NV) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems) or the MEGABASE 1000 DNA sequencing system (Amersham Pharmacia Biotech). Most of the isolates were sequenced according to standard ABI protocols and kits (PE Biosystems) with solution volumes of 0.25×–1.0× concentrations. In the alternative, cDNAs were sequenced using solutions and dyes from Amersham Pharmacia Biotech.

IV Extension of cDNA Sequences

The nucleic acid molecules were extended using a cDNA clone and oligonucleotide primers. One primer was synthesized to initiate 5' extension of the known fragment, and the other, to initiate 3' extension of the known fragment. The initial primers were designed using OLIGO 4.06 software (National Biosciences, Plymouth Minn.), or another appropriate program, to be about 22 to 30 nucleotides in length, to have a GC content of about 50% or more, and to anneal to the target sequence at temperatures of about 68C to about 72C. Any stretch of nucleotides that would result in hairpin structures and primer-primer dimerizations was avoided.

Selected cDNA libraries were used as templates to extend the sequence. If more than one extension was necessary or desired, additional or nested sets of primers were designed. Preferred libraries are ones that have been size-selected to include larger cDNAs. Also, random primed libraries are preferred because they will contain more sequences with the 5' and upstream regions of genes. A randomly primed library is particularly useful if an oligo d(T) library does not yield a full length cDNA. Genomic libraries are useful for extension 5' of the promoter binding region in order to obtain regulatory elements.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B (Incyte Pharmaceuticals): Step 1: 94C, three min; Step 2: 94C, 15 sec; Step 3: 60C, one min; Step 4: 68C, two min; Step 5: Steps 2, 3, and 4 repeated 20 times; Step 6: 68C, five min; Step 7: storage at 4C. In the alternative, the parameters for primer pair T7 and SK+ (Stratagene) were as follows: Step 1: 94C, three min; Step 2: 94C, 15 sec; Step 3: 57C, one min; Step 4: 68C, two min; Step 5: Steps 2, 3, and 4 repeated 20 times; Step 6: 68C, five min; Step 7: storage at 4C.

The concentration of DNA in each well was determined by dispensing 100 μl PICOGREEN quantitation reagent (0.25% reagent in 1×TE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended nucleotide sequences were desalted, concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC 18 vector (Amersham Pharmacia Biotech), treated with Pfu DNA polymerase (Stratagene) to fill-in restriction site overhangs, and transfected into E. coli competent cells. Transformed cells were selected on antibiotic-containing media, and individual colonies were picked and cultured overnight at 37C in 384-well plates in LB/2× carbenicillin liquid media.

The cells were lysed, and DNA was amplified using primers, Taq DNA polymerase (Amersham Pharmacia Biotech) and Pfu DNA polymerase (Stratagene) with the following parameters: Step 1: 94C, three min; Step 2: 94C, 15 sec; Step 3: 60C, one min; Step 4: 72C, two min; Step 5: steps 2, 3, and 4 repeated 29 times; Step 6: 72C, five min; Step 7: storage at 4C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (Amersham Pharmacia Biotech) or the ABI PRISM BIGDYE terminator cycle sequencing kit (PE Biosystems).

V Homology Searching of cDNA Clones and Their Deduced Polypeptides

The nucleic acid molecules of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gorf/b2.html) includes various sequence analysis programs including "blastn", that is used to align a known nucleic acid molecules, BLAST 2 that is used for direct pairwise comparison of either nucleic or amino acid molecules. BLAST programs are commonly used with gap and other parameters set to default settings, e.g.: Matrix: BLOSUM62; Reward for match: 1; Penalty for mismatch: −2; Open Gap: 5 and Extension Gap: 2 penalties; Gap x drop-off: 50; Expect: 10; Word Size: 11; and Filter: on. Identity or similarity may be measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The mammalian nucleic acid molecule of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. No. 08/812,290 and U.S. Ser. No. 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo. http://pfam.wustl.edu/).

The nucleic acid molecule was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the nucleic acid molecules presented in the Sequence Listing have been mapped. Any of the fragments of the nucleic acid molecule encoding NIM1 kinase that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses
Immobilization of Nucleic acid molecules on a Substrate Nucleic acid molecules are applied to a substrate by one of the following methods. A mixture of nucleic acid molecules is fractionated by gel electrophoresis and transferred to a nylon membrane by capillary transfer. Alternatively, the nucleic acid molecules are individually ligated to a vector and inserted into bacterial host cells to form a library. The nucleic acid molecules are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37C for 16 hr. The membrane is removed from the agar and consecutively placed colony side up in 10% SDS, denaturing solution (1.5 M NaCl, 0.5 M NaOH ), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, nucleic acid molecules are amplified from bacterial vectors by thirty cycles of PCR using primers complementary to vector sequences flanking the insert. PCR amplification increases a starting concentration of 1–2 ng nucleic acid to a final quantity greater than 5 μg. Amplified nucleic acids from about 400 bp to about 5000 bp in length are purified using SEPHACRYL-400 beads (Amersham Pharmacia Biotech). Purified nucleic acids are arranged on a nylon membrane manually or using a dot/slot blotting manifold and suction device and are immobilized by denaturation, neutralization, and UV irradiation as described above. Purified nucleic acids are robotically arranged and immobilized on polymer-coated glass slides using the procedure described in U.S. Pat. No. 5,807,522. Polymer-coated slides are prepared by cleaning glass microscope slides (Corning, Acton Mass.) by ultrasound in 0. 1% SDS and acetone, etching in 4% hydrofluoric acid (VWR Scientific Products, West Chester Pa.), coating with 0.05% aminopropyl silane (Sigma Aldrich) in 95% ethanol, and curing in a 110C oven. The slides are washed extensively with distilled water between and after treatments. The nucleic acids are arranged on the slide and then immobilized by exposing the array to UV irradiation using a STRATALINKER UV-crosslinker a(Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60C; then the arrays are washed in 0.2% SDS and rinsed in distilled water as before .

Probe Preparation for Membrane Hybridization

Hybridization probes derived from the nucleic acid molecules of the Sequence Listing are employed for screening cDNAs, mRNAs, or genomic DNA in membrane-based hybridizations. Probes are prepared by diluting the nucleic acid molecules to a concentration of 40–50 ng in 45 $\mu$l TE buffer, denaturing by heating to 100C for five min, and briefly centrifuging. The denatured nucleic acid molecule is then added to a REDIPRIME tube (Amersham Pharmacia Biotech), gently mixed until blue color is evenly distributed, and briefly centrifuged. Five $\mu$l of [$^{32}$P]dCTP is added to the tube, and the contents are incubated at 37C for 10 min. The labeling reaction is stopped by adding 5 $\mu$l of 0.2M EDTA, and probe is purified from unincorporated nucleotides using a PROBEQUANT G-50 microcolumn (Amersham Pharmacia Biotech). The purified probe is heated to 100C for five min, snap cooled for two min on ice, and used in membrane-based hybridizations as described below.

Probe Preparation for Polymer Coated Slide Hybridization

Hybridization probes derived from mRNA isolated from samples are employed for screening nucleic acid molecules of the Sequence Listing in array-based hybridizations. Probe is prepared using the GEMbright kit (Incyte Pharmaceuticals) by diluting mRNA to a concentration of 200 ng in 9 $\mu$l TE buffer and adding 5 $\mu$l 5× buffer, 1 $\mu$l 0.1 M DTT, 3 $\mu$l Cy3 or Cy5 labeling mix, 1 $\mu$l RNase inhibitor, 1 $\mu$l reverse transcriptase, and 5 $\mu$l 1× yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37C for two hr. The reaction mixture is then incubated for 20 min at 85C, and probes are purified using two successive CHROMA SPIN+TE 30 columns (Clontech, Palo Alto Calif.). Purified probe is ethanol precipitated by diluting probe to 90 $\mu$l in DEPC-treated water, adding 2 $\mu$l 1 mg/ml glycogen, 60 $\mu$l 5 M sodium acetate, and 300 $\mu$l 100% ethanol. The probe is centrifuged for 20 min at 20,800×g, and the pellet is resuspended in 12 $\mu$l resuspension buffer, heated to 65C for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1× high phosphate buffer (0.5 M NaCl, 0.1 M $Na_2HPO_4$, 5 mM EDTA, pH 7) at 55C for two hr. The probe, diluted in 15 ml fresh hybridization solution, is then added to the membrane. The membrane is hybridized with the probe at 55C for 16 hr. Following hybridization, the membrane is washed for 15 min at 25C in 1 mM Tris (pH 8.0), 1% Sarkosyl, and four times for 15 min each at 25C in 1 nM Tris (pH 8.0). To detect hybridization complexes, XOMAT-AR film (Eastman Kodak, Rochester N.Y.) is exposed to the membrane overnight at −70C, developed, and examined visually.

Polymer Coated Slide-based Hybridization

Probe is heated to 65C for five min, centrifuged five min at 9400 rpm in a 5415C microcentrifuge (Eppendorf Scientific, Westbury N.Y.), and then 18 $\mu$l is aliquoted onto the array surface and covered with a coverslip. The arrays are transferred to a waterproof chamber having a cavity just slightly larger than a microscope slide. The chamber is kept at 100% humidity internally by the addition of 140 $\mu$l of 5×SSC in a corner of the chamber. The chamber containing the arrays is incubated for about 6.5 hr at 60C. The arrays are washed for 10 min at 45C in 1×SSC, 0.1% SDS, and three times for 10 min each at 45C in 0.1×SSC, and dried.

Hybridization reactions are performed in absolute or differential hybridization formats. In the absolute hybridization format, probe from one sample is hybridized to array elements, and signals are detected after hybridization complexes form. Signal strength correlates with probe MRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20× microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R 1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for CyS. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Pharmaceuticals).

VIII Northern Analysis

Electronic

Computer techniques applying BLAST were used to search for identical or related molecules in nucleotide databases such as GenBank or LIFESEQ databases (Incyte Pharmaceuticals). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

The results of the electronic northern performed at a product score of 70 are shown in FIG. 2. Analysis involved the categorization of cDNA libraries by system, organ/tissue and cell type. The categories included cardiovascular system, connective tissue (specifically cancerous breast fibroblasts), digestive system, embryonic structures, endocrine system, exocrine glands, female and male genitalia (specifically cancerous prostate), germ cells, hemic and immune system, liver, musculoskeletal system, nervous system, pancreas, respiratory system, sense organs, skin, stomatognathic system, unclassified/mixed, and the urinary tract For each category, the number of libraries expressing the sequence was counted and shown over the total number of libraries in that category.

Quantitative PCR

Quantitative PCR was used to examine expression of human NIM1 kinase in various cell lines and tissues. The cell lines, obtained from sources such as ATCC, were H460 human non-small cell lung carcinoma, A2780 human ovarian carcinoma line, A375 human melanoma cell line, HDF human dermal fibroblasts, HELA human cervix carcinoma, DU145 androgen-independent prostate carcinoma cell line, MDA-MB231 human mammary tumor cells, U87 glioblastoma tumor cells, and BX-PC3 pancreatic cancer cells. The cell lines were plated in culture dishes and grown in RPMI supplemented with 10% fetal bovine serum, 2 mM glutamine at 37C in 5% $CO_2$ until they were 90% confluent. The tissues, brain, colon, uterus and placenta, were obtained as MTN blots (Human I, II, III, and IV) from Clontech.

Northern analysis was by quantitative PCR as performed using the ABI PRISM 7700 Sequencing system and TAQ-MAN assay reagents (TAQMAN Universal PCR Master mix) and technology according to manufacturer instructions (all PE Biosystems). All reactions were performed in triplicate.

The primers used in the reaction included SEQ ID NOs:37–39. Relative quantification was done using 18s RNA as the standard. This linearity of this standardization procedure was described in Spiess and Ivell (1999; Biotechniques 26:46–50, incorporated herein by reference).

IX Complementary Nucleic Acid Molecules

Molecules complementary to the nucleic acid molecule, or a fragment thereof, are used to detect, decrease, or inhibit gene expression. Although use of oligonucleotides comprising from about 15 to about 30 base pairs is described, the same procedure is used with larger or smaller fragments or their derivatives (PNAs). Appropriate oligonucleotides are selected using OLIGO 4.06 software (National Biosciences). To inhibit transcription by preventing promoter binding, a complementary oligonucleotide is designed to bind to the most unique 5' sequence, most preferably about 10 nucleotides before the initiation codon of the open reading frame. To inhibit translation, a complementary oligonucleotide is designed to prevent ribosomal binding to the mRNA encoding the mammalian polypeptide.

In addition to using antisense molecules constructed to interrupt transcription or translation, modifications of gene expression can be obtained by designing antisense molecules to genomic sequences (such as enhancers or introns) or even to trans-acting regulatory genes. Similarly, antisense inhibition can be achieved using Hogeboom base-pairing methodology, also known as "triple helix" base pairing. Antisense molecules involved in triple helix pairing compromise the ability of the double helix to open sufficiently for the binding of polymerases, transcription factors, or regulatory molecules.

Such antisense molecules are placed in expression vectors and used to transform preferred cells or tissues. This may include introduction of the expression vector into a cell line to test efficacy; into an organ, tumor, synovial cavity, or the vascular system for transient or short term therapy; or into a stem cell or other reproducing lineage for long term or stable gene therapy. Transient expression may last for a month or more with a non-replicating vector and for three months or more if appropriate elements for inducing vector replication are used in the transformation/expression system.

Stable transformation of appropriate dividing cells with a vector encoding the antisense molecule can produce a transgenic cell line, tissue, or organism (U.S. Pat. No. 4,736,866). Those cells that assimilate and replicate sufficient quantities of the vector to allow stable integration also produce enough antisense molecules to compromise or entirely eliminate activity of the nucleic acid molecule encoding the manmmalian protein.

X Expression of NIM1 Kinase

Expression of the human NIM1 kinase was achieved using monkey and insect cell-based expression systems. The cDNA was purified using QIAPREP spin miniprep kit and PLASMID MAXI kit (both Qiagen) accordingly to the manufacturer's instructions.

For transient expression, the cDNA was cloned into the pcDNA3.1 (-)/myc-His B vector (Invitrogen, Carlsbad Calif.), and the vector pcDNA3-Nim1 was transformed into COS 1-1 cells using $CaPO_4$ transfection kit 2-463335 (Eppendorf—5 Prime, Boulder Colo). $4 \times 10^6$ cells were seeded in 10 cm tissue culture dishes 24 hr before transformation. On the day of transformation, CaPO4-DNA precipitate was obtained using 500 ml 2x DNA precipitation buffer, 62 ml M $CaCL_2$, 10 mg (10 ml) pcDNA3-Nim1, and 428 ml water. The mixture was incubated at room temperature for 20 min and then slowly added to 9 ml of culture medium (DMEM, 10% fetal calf serum, 2 mM glutamine, 10 mg/ml penicillin and 10 mg/ml streptomycin). Cells were incubated at 37C at 5% $CO_2$ for 4 h. The medium was replaced with fresh medium, and cells were incubated for 48 additional hours.

Sf21 insect cells were cotransformed according instructions supplied with the BaculoGold transfection kit (BD Pharmingen, San Diego Calif.). $2\times10^6$ cells were seeded in one 6 cm tissue culture dish and incubated at 27C for 15 min. 4 mg (4 ml) of pVL 1392/GST-NIM1 expression vector were combined with 0.5 mg (0.5 ml) of BaculoGold DNA and incubated at room temperature for 5 min. The cells' medium (TNM-FH) was removed and replaced with 1 ml of Buffer A. The DNA mixture was diluted in 1 ml of Buffer B and added drop by drop to the cotransfection plate. After the plate was incubated at 27C for 4 hours, the medium was replaced, and the cells were incubated for 5 days.

The recombinant viruses were subjected to three cycles of amplification to obtain a $10^7$ pfu/ml viral stock. $1.2\times10^7$ Sf21 insect cells were infected with 10 ml of viral stock and incubated at 27C. After 3 days, the cells were lysed, and the protein was purified.

XI Protein Purification

His-purification

COS-1 cells were centrifuged at 1000 rpm, resuspended in 4 ml of lysis buffer (5 mM imidazole +0.5 mM NaCl +20 mM $Na2HPO_4$+Complete protease inhibitor cocktail tablets, (Roche Molecular Biochemicals, Indianapolis Ind.)) and sonicated. The soluble fraction was recovered by centrifugation at 10000 rpm for 10 min at 4C. The recombinant Nimrl kinase was purified by immobilized metal ion affinity chromatography (IMAC, Invitrogen) according to manufacturer instructions. Purity was determined by SDS-polyacrylamide gel electrophoresis (SDS-PAGE) and Coomassie blue staining. Protein concentration was determined using the Bradford method.

GST-purification

Sf21 cells were centrifuged at 800 rpm, resuspended in 10 ml of lysis buffer (PBS+1 mM orthovanadate+20 mM DTT+ Complete protease inhibitor cocktail tablets (Roche Molecular Biochemicals)), and sonicated. The soluble fraction was recovered by centrifugation at 10000 rpm for 10 min at 4C. The recombinant Nim1 kinase was purified by affinity chromatography on glutathione-SEPHAROSE resin (Amersham Pharmacia Biotech) following the manufacturer instructions. Purity was determined using SDS-PAGE followed by Coomassie blue staining. Protein concentration was determined by the Bradford method.

For Western blot analysis, proteins were separated by SDS-PAGE and analyzed by immunoblotting (with either GST-HRP conjugated antibody or His-HRP conjugated antibody, Santa Cruz Biotechnology) using standard materials and techniques (ECL, Amersham Pharmacia Biotech).

XII Characterization of the Protein

In vitro translation of Incyte Clone number 3317608 was accomplished using the TNT T7 quick coupled transcriptional translational system (Promega) and the manufacturer's instructions. SDS-PAGE analysis revealed the presence of a 48 kd protein. The size of the protein was confirmed by expressing pcDNA3-Nim1 as a template.

As previously described, Nim1 kinase was expressed in both mammalian and insect cells. The purified protein was subjected to SDS-PAGE and revealed a 50 kd protein (including myc-His tag) and an 80 kd protein (including GST tag) respectively.

XIII Human NIM1 Kinase Assay

An in vitro kinase assay was performed by incubating 100 ng of recombinant Nim1-GST with 2 μg of myelin basic protein (MBP) or histone (HIST) in 20 μl of kinase buffer (50 mM Hepes pH 7.5, 3 mM $MgCl_2$ and $MnCl_2$, 10 mM DTT and 6 μM NaOVa) containing 10 μCi of [y-$^{32}$P]-ATP (3000 Ci/mmol; Amersham Pharmaca Biotech) for 30 min at 37C. The reaction was stopped by adding sample buffer and heating to 100C for 5 min. Samples were analyzed by SDS-PAGE, the gels were dried and subjected to autoradiographic analysis.

XIV Production of NIM1 kinase Specific Antibodies

NIM1 kinase is purified using polyacrylamide gel electrophoresis and used to immunize mice or rabbits. Antibodies are produced using the protocols below. Alternatively, the amino acid sequence of NIM1 kinase is analyzed using LASERGENE software (DNASTAR) to determine regions of high immunogenicity. An immunogenic epitope, usually found near the C-terminus or in a hydrophilic region is selected, synthesized, and used to raise antibodies. Typically, epitopes of about 15 residues in length are produced using an ABI 431A peptide synthesizer (PE Biosystems) using Fmoc-chemistry and coupled to KLH (Sigma-Aldrich) by reaction with N-maleimidobenzoyl-N-hydroxysuccinimide ester to increase immunogenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XV Purification of Naturally Occurring Protein Using Specific Antibodies

Naturally occurring or recombinant mammalian protein is substantially purified by immunoaffinity chromatography using antibodies specific for the protein. An immunoaffinity column is constructed by covalently coupling the antibody to CNBr-activated SEPHAROSE resin (Amersham Pharmacia Biotech). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XVI Screening Molecules for Specific Binding with the Nucleic Acid Molecule or Protein The nucleic acid molecule, or fragments thereof, or the protein, or portions thereof, are labeled with $^{32}$P-dCTP, Cy3-dCTP, or Cy5-dCTP (Amersham Pharmacia Biotech), or with BIODIPY or FITC (Molecular Probes, Eugene Oreg.), respectively. Libraries of candidate molecules or compounds previously arranged on a substrate are incubated in the presence of labeled nucleic acid molecule or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XVII Two-Hybrid Screen

A yeast two-hybrid system, MATCHMAKER LexA Two-Hybrid system (Clontech Laboratories, Palo Alto Calif.), is used to screen for peptides that bind the mammalian protein of the invention. A nucleic acid molecule encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30C until the colonies have grown up and can be counted. The colonies are pooled in a minimal volume of 1× TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30C. A sample of the culture is plated on SD/-Trp/-Ura media and incubated at 30C until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a nucleic acid molecule encoding a protein that physically interacts with the mammalian protein, can be isolated from the yeast cells and characterized.

All patents and publications mentioned in the specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

SEQUENCE LISTING

```
<160> NUMBER OF SEQ ID NOS: 39

<210> SEQ ID NO 1
<211> LENGTH: 2060
<212> TYPE: DNA
<213> ORGANISM: Homo sapiens
<220> FEATURE:
<221> NAME/KEY: misc_feature
<223> OTHER INFORMATION: Incyte Clone No: 3317608CB1

<400> SEQUENCE: 1
cagagatgag atcccgcagc agggacgtgg gggcctccca ggggcattta cgcaccagag      60
tgcaagattc tctggccatc aagggaaata gcaaacagaa gcctttgtcc tgggcacag     120 ccacctacca caaagcatca gactccacgt ctggccagaa agttcctgga gtcccatcag    180
gccagtgggt atgtaacatg tgcctaattg tacagctaga gcctgcaagt tcaacgtgag    240
ggaaggtggg aaatgtcttg agtgaggcga gcagctcctg gctgggctgg gcagactcag    300
ctaccacgtt cactgccttc ctctcactaa agccgagagg gaggctgctc agctctcagg    360
aaaactcttt tgaaccctgg gcacctgctg tcctcagttg gcatctccca ccctctgagc    420
ctcttctgct cctgcacaac ctgcctcttc gctgagatgg agacgtgagc ccccgtggac    480
gatgactgca gtgtatatga atggaggtgg cctggtgaac ccccactatg cccggtggga    540
tcggcgcgac agtgtagaaa gtggctgtca gaccgagagt agcaaggtgg gtgaggaggg    600
acagccccgc cagctgacgc ccttcgagaa actgacacag gacatgtccc aggatgagaa    660
```

-continued

| | |
|---|---|
| ggtggtgagg gagatcacgc tggggaaacg gataggcttc taccgaattc gaggggaaat | 720 |
| cggaagtgga aacttctccc aagtgaagct tgggattcac tccctaacca agaaaaggt | 780 |
| ggccattaag atcctggaca agaccaagtt agaccagaaa acccagaggc tactatcccg | 840 |
| agaaatctcc agcatggaaa agctgcacca tcccaacatc atccgccttt acgaagtggt | 900 |
| ggagaccta tccaagctgc acttggtgat ggagtatgca gggggtgggg agctcttcgg | 960 |
| aaaaattagc actgagggga agctctctga accagaaagc aagctcatct tctcccagat | 1020 |
| tgtgtctgcc gtgaagcaca tgcatgaaaa ccaaattatt catagagatc tgaaagcaga | 1080 |
| aaatgtattc tataccagta atacttgtgt gaaggtgggc gattttggat tcagcacagt | 1140 |
| aagcaaaaaa ggtgaaatgc tgaacacttt ctgtgggtct cctccctacg ctgcgcctga | 1200 |
| actcttccgg gacgagcact acatcggcat ttacgtggat atctgggcct tgggggtgct | 1260 |
| tttgtacttc atggtgactg gcaccatgcc atttcgggca gaaaccgtgg ccaaactaaa | 1320 |
| aaagagcatc ctcgagggca catacagtgt accgccgcac gtgtcagagc cctgccaccg | 1380 |
| actcatccga ggagtccttc agcagatccc cacggagagg tacggaatcg actgcatcat | 1440 |
| gaatgatgaa tggatgcaag gggtgccata ccctacacct ttggaacctt ccaactgga | 1500 |
| tcccaaacat ttgtcggaaa ccagcactct caaggaagaa gaaatgagg tcaaaagcac | 1560 |
| tttagaacat ttgggcatta cagaagagca tattcgaaat aaccaaggga gagatgctcg | 1620 |
| cagctcaatc acagggtct atagaattat tttacataga gtccaaagga agaaggcttt | 1680 |
| ggaaagtgtc ccagtcatga tgctaccaga ccctaaagaa agagacctca aaaagggtc | 1740 |
| ccgtgtctac agaggataa acacacatc caaattttgc tcgattttat aaattgcact | 1800 |
| agactgcttg taactaacca agatgattgt tgctgcttct aaatttttt caaggacaac | 1860 |
| ttgagtggag acattttgt aattttaaa taaacttaaa tttgagatat gcaaaaaaa | 1920 |
| aaaaaaaag gcggccgcc gactagtgag ctcgtcgacc cgggaattaa ttccggaccg | 1980 |
| gtacctgcag gcgtaccagc tttccctata gtggagtccg tattaaactt ggccgtaatc | 2040 |
| atggcataac ttgttccctg | 2060 |

<210> SEQ ID NO 2
<211> LENGTH: 436
<212> TYPE: PRT
<213> ORGANISM: Homo sapiens
<220> FEATURE:
<221> NAME/KEY: misc_feature
<223> OTHER INFORMATION: Incyte ID No: 3317608CD1

<400> SEQUENCE: 2

Met Thr Ala Val Tyr Met Asn Gly Gly Gly Leu Val Asn Pro His
1               5                   10                  15

Tyr Ala Arg Trp Asp Arg Arg Asp Ser Val Glu Ser Gly Cys Gln
                20                  25                  30

Thr Glu Ser Ser Lys Val Gly Glu Glu Gly Gln Pro Arg Gln Leu
                35                  40                  45

Thr Pro Phe Glu Lys Leu Thr Gln Asp Met Ser Gln Asp Glu Lys
                50                  55                  60

Val Val Arg Glu Ile Thr Leu Gly Lys Arg Ile Gly Phe Tyr Arg
                65                  70                  75

Ile Arg Gly Glu Ile Gly Ser Gly Asn Phe Ser Gln Val Lys Leu
                80                  85                  90

Gly Ile His Ser Leu Thr Lys Glu Lys Val Ala Ile Lys Ile Leu
                95                  100                 105

```
Asp Lys Thr Lys Leu Asp Gln Lys Thr Gln Arg Leu Leu Ser Arg
            110                 115                 120

Glu Ile Ser Ser Met Glu Lys Leu His His Pro Asn Ile Ile Arg
            125                 130                 135

Leu Tyr Glu Val Val Glu Thr Leu Ser Lys Leu His Leu Val Met
            140                 145                 150

Glu Tyr Ala Gly Gly Glu Leu Phe Gly Lys Ile Ser Thr Glu
            155                 160                 165

Gly Lys Leu Ser Glu Pro Glu Ser Lys Leu Ile Phe Ser Gln Ile
            170                 175                 180

Val Ser Ala Val Lys His Met His Glu Asn Gln Ile Ile His Arg
            185                 190                 195

Asp Leu Lys Ala Glu Asn Val Phe Tyr Thr Ser Asn Thr Cys Val
            200                 205                 210

Lys Val Gly Asp Phe Gly Phe Ser Thr Val Ser Lys Lys Gly Glu
            215                 220                 225

Met Leu Asn Thr Phe Cys Gly Ser Pro Pro Tyr Ala Ala Pro Glu
            230                 235                 240

Leu Phe Arg Asp Glu His Tyr Ile Gly Ile Tyr Val Asp Ile Trp
            245                 250                 255

Ala Leu Gly Val Leu Leu Tyr Phe Met Val Thr Gly Thr Met Pro
            260                 265                 270

Phe Arg Ala Glu Thr Val Ala Lys Leu Lys Lys Ser Ile Leu Glu
            275                 280                 285

Gly Thr Tyr Ser Val Pro Pro His Val Ser Glu Pro Cys His Arg
            290                 295                 300

Leu Ile Arg Gly Val Leu Gln Gln Ile Pro Thr Glu Arg Tyr Gly
            305                 310                 315

Ile Asp Cys Ile Met Asn Asp Glu Trp Met Gln Gly Val Pro Tyr
            320                 325                 330

Pro Thr Pro Leu Glu Pro Phe Gln Leu Asp Pro Lys His Leu Ser
            335                 340                 345

Glu Thr Ser Thr Leu Lys Glu Glu Asn Glu Val Lys Ser Thr
            350                 355                 360

Leu Glu His Leu Gly Ile Thr Glu Glu His Ile Arg Asn Asn Gln
            365                 370                 375

Gly Arg Asp Ala Arg Ser Ser Ile Thr Gly Val Tyr Arg Ile Ile
            380                 385                 390

Leu His Arg Val Gln Arg Lys Lys Ala Leu Glu Ser Val Pro Val
            395                 400                 405

Met Met Leu Pro Asp Pro Lys Glu Arg Asp Leu Lys Lys Gly Ser
            410                 415                 420

Arg Val Tyr Arg Gly Ile Arg His Thr Ser Lys Phe Cys Ser Ile
            425                 430                 435

Leu

<210> SEQ ID NO 3
<211> LENGTH: 1051
<212> TYPE: DNA
<213> ORGANISM: Homo sapiens
<220> FEATURE:
<221> NAME/KEY: misc_feature
<223> OTHER INFORMATION: Incyte Template No: 200700.1

<400> SEQUENCE: 3
```

```
gctgcaccat cccaacatca tccgccttta cgaagtggtg gagaccctat ccaagctgca    60
cttggtgatg gagtatgcag ggggtgggga gctcttcgga aaaattagca ctgaggggaa   120
gctctctgaa ccagaaagca agctcatctt ctcccagatt gtgtctgccg tgaagcacat   180
gcatgaaaac caaattattc atagagatct gaaagcagaa aatgtattct ataccagtaa   240
tacttgtgtg aaggtgggcg attttggatt cagcacagta agcaaaaaag gtgaaatgct   300
gaacactttc tgtgggtctc ctccctacgc tgcgcctgaa ctcttccggg acgagcacta   360
catcggcatt tacgtggata tctgggcctt gggggtgctt ttgtacttca tggtgactgg   420
caccatgcca tttcgggcag aaaccgtggc caaactaaaa agagcatccc tcgagggcac   480
atacagtgta ccgccgcacg tgtcagagcc ctgccaccga ctcatccgag gagtccttca   540
gcagatcccc acggagaggt acggaatcga ctgcatcatg aatgatgaat ggatgcaagg   600
ggtgccatac cctacacctt tggaaccttt ccaactggat cccaaacatt tgtcggaaac   660
cagcactctc aaggaagaag aaaatgaggt caaaagcact ttagaacatt tgggcattac   720
agaagagcat attcgaaata accaaggaga gatgctcgc agctcaatca gggggtcta    780
tagaattatt ttacatagag tccaaaggaa aaggctttg gaaagtgtcc cagtcatgat   840
gctaccagac cctaaagaaa gagacctcaa aaaagggtcc cgtgtctaca gagggataag   900
acacacatcc aaattttgct cgattttata aattgcacta gactgcttgt aactaaccaa   960
gatgattgtt gctgcttcta aatttttttc aaggacaact tgagtggaga catttttgta  1020
atttttaaat aaacttaaat ttgagatatg c                                 1051

<210> SEQ ID NO 4
<211> LENGTH: 1507
<212> TYPE: DNA
<213> ORGANISM: Homo sapiens
<220> FEATURE:
<221> NAME/KEY: misc_feature
<223> OTHER INFORMATION: Incyte Clone No: 670279CB1

<400> SEQUENCE: 4
gagcctcttc tgctcctgca caacctgcct cttcgctgag atggagacgt gagccccgt    60
ggacgatgac tgcagtgtat atgaatggag gtggcctggt gaaccccca ctatgccgg    120
tgggatcggc gcgacagtgt agaaagtggc tgtcagaccg agagtagcaa ggtgggtgag   180
gagggacagc cccgccagct gacgcccttc gagaaactga cacaggacat gtcccaggat   240
gagaaggtgg tgagggagat cacgctgggg aaacggatag gcttctaccg aattcgaggg   300
gaaatcggaa gtgaaaactt ctcccaagtg aagcttggga ttcactccct aaccaaagaa   360
aaggtggcca ttaagatcct ggacaagacc aagttagacc agaaaaccca gaggctacta   420
tcccgagaaa tctccagcat ggaaaagctg caccatccca acatcatccg cctttacgaa   480
gtggtggaga cccctatccaa gctgcacttg gtgatggagt atgcagggg tggggagctc   540
ttcggaaaaa ttagcactga ggggaagctc tctgaaccag aaagcaagct catcttctcc   600
cagattgtgt ctgccgtgaa gcacatgcat gaaaaccaaa ttattcatag agatctgaaa   660
gcagaaaatg tattctatac cagtaatact tgtgtgaagg tgggcgattt tggattcagc   720
acagtaagca aaaaggtga atgctgaac actttctgtg gtctcctcc ctacgctgcg    780
cctgaactct tccgggacga gcactacatc ggcatttacg tggatatctg ggccttgggg   840
gtgcttttgt acttcatggt gactggcacc atgccatttc gggcagaaac cgtggccaaa   900
ctaaaaaaga gcatcctcga gggcacatac agtgtaccgc cgcacgtgtc agagccctgc   960
```

-continued

```
caccgactca tccgaggagt ccttcagcag atccccacgg agaggtacgg aatcgactgc    1020
atcatgaatg atgaatggat gcaagggtg ccataccta cacctttgga accttttccaa     1080 ctggatccca aacatttgtc ggaaaccagc actctcaagg aagaagaaaa tgaggtcaaa    1140
agcactttag aacatttggg cattacagaa gagcatattc gaataaacca agggagagat   1200
gctcgcagct caatcacagg ggtctataga attattttac atagagtcca aaggaagaag   1260
gctttggaaa gtgtcccagt catgatgcta ccagacccta agaaagaga cctcaaaaaa    1320 gggtcccgtg tctacagagg gataagacac acatccaaat tttgctcgat tttataaatt   1380
gcactagact gcttgtaact aaccaagatg attgttgctg cttctaaatt tttttcaagg   1440
acaacttgag tggagacatt tttgtaattt ttaaataaac ttaaatttga gatatgcaaa   1500
aaaaaaa                                                              1507
```

<210> SEQ ID NO 5
<211> LENGTH: 258
<212> TYPE: DNA
<213> ORGANISM: Homo sapiens
<220> FEATURE:
<221> NAME/KEY: misc_feature
<223> OTHER INFORMATION: Incyte Clone No: 3317608H1

<400> SEQUENCE: 5

```
cagagatgag atcccgcagc agggacgtgg gggcctccca ggggcattta cgcaccagag     60
tgcaagattc tctggccatc aagggaaata gcaaacagaa gcctttgtcc tggggcacag   120
ccacctacca caaagcatca gactccacgt ctggccagaa agttcctgga gtcccatcag   180
gccagtgggt atgtaacatg tgcctaattg tacagctaga gcctgcaagt tcaacgtgag   240
ggaaggtggg aaatgtct                                                  258
```

<210> SEQ ID NO 6
<211> LENGTH: 290
<212> TYPE: DNA
<213> ORGANISM: Homo sapiens
<220> FEATURE:
<221> NAME/KEY: misc_feature
<223> OTHER INFORMATION: Incyte Clone No: 4313713H1

<400> SEQUENCE: 6

```
ggagtatgca gggggtgggg agctcttcgg aaaaattagt actgagggga agctctctga     60
accagaaagc aagctcatct tctcccagat tgtgtctgcc gtgaagcaca tgcatgaaaa   120
ccaaattatt catagagatc tgaaagcaga aaatgtttct ataccagtaa tacttgtgtg   180
aaggtgggcg attttggatt cagcacagta agcaaaaaag gtgaaatgct gaacatttct   240
gtgggtctcc tccctacgct gcgctgaact cttccgggga cgagcattac                290
```

<210> SEQ ID NO 7
<211> LENGTH: 256
<212> TYPE: DNA
<213> ORGANISM: Homo sapiens
<220> FEATURE:
<221> NAME/KEY: misc_feature
<223> OTHER INFORMATION: Incyte Clone No: 4617082H1
<220> FEATURE:
<221> NAME/KEY: unsure
<222> LOCATION: 194, 241
<223> OTHER INFORMATION: a, t, c, g, or other

<400> SEQUENCE: 7

```
agcaaaaaag gtgaaatgct gaacactttc tgtgggtctc ctccctacgc tgcgcctgaa     60
```

```
ctcttccggg acgagcacta catcggcatt tacgtggata tctgggcctt gggggtgctt    120
ttgtacttca tggtgactgg caccatgcca tttcgggcag aaaccgtggc caaactaaaa    180
aagagcatcc tcgnggggcac atacagtgta ccgccgcacg tgtcagagcc ctgccaccga   240
ntcatccgag gagtct                                                    256
```

```
<210> SEQ ID NO 8
<211> LENGTH: 250
<212> TYPE: DNA
<213> ORGANISM: Homo sapiens
<220> FEATURE:
<221> NAME/KEY: misc_feature
<223> OTHER INFORMATION: Incyte Clone No: 4711644H1
<220> FEATURE:
<221> NAME/KEY: unsure
<222> LOCATION: 228
<223> OTHER INFORMATION: a, t, c, g, or other

<400> SEQUENCE: 8
```

```
ctcactaaag ccgagaggga ggctgctcag ctctcaggaa aactcttttg aaccctgggc    60
acctgctgtc ctcagttggc atctcccacc ctctgagcct cttctgctcc tgcacaacct   120
gcctcttcgc tgagatggag acgtgagccc ccgtggacga tgactgcagt gtatatgaat   180
ggaggtggcc tggtgaaccc ccactatgcc cggtgggatc ggcgcganag tgtagaaagt   240
ggctgtcaga                                                          250
```

```
<210> SEQ ID NO 9
<211> LENGTH: 243
<212> TYPE: DNA
<213> ORGANISM: Homo sapiens
<220> FEATURE:
<221> NAME/KEY: misc_feature
<223> OTHER INFORMATION: Incyte Clone No: 2286324H1

<400> SEQUENCE: 9
```

```
gaattatttt acatagagtc caaaggaaga aggctttgga aagtgtccca gtcatgatgc    60
taccagaccc taaagaaaga gacctcaaaa aagggtcccg tgtctacaga gggataagac   120
acacatccaa attttgctcg attttataaa ttgcactaga ctgcttgtaa ctaaccaaga   180
tgattgttgc tgcttctaaa ttttttttcaa ggacaacttg agtggagaca ttttttgtaat  240 ttt                                                                 243
```

```
<210> SEQ ID NO 10
<211> LENGTH: 232
<212> TYPE: DNA
<213> ORGANISM: Homo sapiens
<220> FEATURE:
<221> NAME/KEY: misc_feature
<223> OTHER INFORMATION: Incyte Clone No: 2286816H1

<400> SEQUENCE: 10
```

```
gaattatttt acatagagtc caaaggaaga aggctttgga aagtgtccca gtcatgatgc    60
taccagaccc taaagaaaga gacctcaaaa aagggtcccg tgtctacaga gggataagac   120
acacatccaa attttgctcg attttataaa ttgcactaga ctgcttgtaa ctaaccaaga   180
tgattgttgc tgcttctaaa ttttttttcaa ggacaacttg agtggagaca tt          232
```

```
<210> SEQ ID NO 11
<211> LENGTH: 88
<212> TYPE: DNA
<213> ORGANISM: Homo sapiens
```

```
<220> FEATURE:
<221> NAME/KEY: misc_feature
<223> OTHER INFORMATION: Incyte Clone No: 2287217H1
<220> FEATURE:
<221> NAME/KEY: unsure
<222> LOCATION: 4
<223> OTHER INFORMATION: a, t, c, g, or other

<400> SEQUENCE: 11
caanagaaag aaacctcaaa aaagggtccc gtgtctacag agggataaga cacacatcca      60
aattttgctc gattttataa attgcact                                        88

<210> SEQ ID NO 12
<211> LENGTH: 270
<212> TYPE: DNA
<213> ORGANISM: Homo sapiens
<220> FEATURE:
<221> NAME/KEY: misc_feature
<223> OTHER INFORMATION: Incyte Clone No: 2286816R6
<220> FEATURE:
<221> NAME/KEY: unsure
<222> LOCATION: 76
<223> OTHER INFORMATION: a, t, c, g, or other

<400> SEQUENCE: 12
gaattatttt acatagagtc caaaggaaga aggctttgga aagtgtccca gtcatgatgc      60
taccagaccc taaagnaaga gacctcaaaa aagggtcccg tgtctacaga gggataagac     120
acacatccaa attttgctcg attttataaa ttgcactaga ctgcttgtaa ctaaccaaga     180
tgattgttgc tgcttctaaa ttttttttcaa ggacaacttg agtggagaca tttttgtaat    240
tttttaaata aacttaaatt tgagatatgc                                     270

<210> SEQ ID NO 13
<211> LENGTH: 230
<212> TYPE: DNA
<213> ORGANISM: Homo sapiens
<220> FEATURE:
<221> NAME/KEY: misc_feature
<223> OTHER INFORMATION: Incyte Clone No: 2286816T6

<400> SEQUENCE: 13
tgtctccact caagttgtcc ttgaaaaaaa tttagaagca gcaacaatca tcttggttag      60
ttacaagcag tctagtgcaa tttataaaat cgagcaaaat ttggatgtgt gtcttatccc     120
tctgtagaca cgggaccctt ttttgaggtc tctttcttta gggtctggta gcatcatgac     180
tgggacactt tccaaagcct tcttcctttg gactctatgt aaaataattc                230

<210> SEQ ID NO 14
<211> LENGTH: 468
<212> TYPE: DNA
<213> ORGANISM: Homo sapiens
<220> FEATURE:
<221> NAME/KEY: misc_feature
<223> OTHER INFORMATION: Incyte Clone No: 3317608T6
<220> FEATURE:
<221> NAME/KEY: unsure
<222> LOCATION: 393
<223> OTHER INFORMATION: a, t, c, g, or other

<400> SEQUENCE: 14
tctccactca agttgtcctt gaaaaaaatt tagaagcagc aacaatcatc ttggttagtt       60
acaagcagtc tagtgcaatt tataaaatcg agcaaaattt ggatgtgtgt cttatccctc     120
tgtagacacg ggaccctttt ttgaggtctc tttctttagg gtctggtagc atcatgactg     180
```

-continued

```
ggacactttc caaagccttc ttcctttgga ctctatgtaa aataattcta tagaccnctg      240
tgattgagct gcgagcatct ctcccttggt tatttcgaat atgctcttct gtaatgccca      300
aatgttctaa agtgcttttg acctcatttt cttcttcctt gagagtgctg gtttccgaca      360
aatgtttggg atccagttgg aaagggtcca aangtgtaag gtatggcacc ccttgcatcc      420
attcatcatt catgatgcag tcgattccgt aactctccgt gggggatc                   468
```

<210> SEQ ID NO 15
<211> LENGTH: 485
<212> TYPE: DNA
<213> ORGANISM: Homo sapiens
<220> FEATURE:
<221> NAME/KEY: misc_feature
<223> OTHER INFORMATION: Incyte Clone No: 4201896T6

<400> SEQUENCE: 15

```
ttcactaatt acaaaaatgt ctccactcaa gttgtccttg acaaaaattt agaagcagca      60
acaatcatct tggttagtta caagcagtct agtgcaattt ataaaatcga gcaaaatttg      120
gatgtgtgtc ttatccctct gtagacacgg gaccctttt tgaggtctct ttctttaggg       180
tctggtagca tcatgactgg gacactttcc aaagccttct cctttggac tctatgtaaa       240 ataattctat agaccctgt gattgagctg cgagcatctc tcccttggtt atttcgaata       300
tgctcttctg taatgcccaa atgttctaaa gtgcttttga cctcattttc ttcttccttg      360
agagtgctgg tttccgacca atgtttggga tccagttgga aaggttccaa aggtgtaggg      420
tatggcaccc cttgcctcca ttcatcattc ctgatgccgt cgattccgta cctctccgtg      480
gggat                                                                  485
```

<210> SEQ ID NO 16
<211> LENGTH: 423
<212> TYPE: DNA
<213> ORGANISM: Homo sapiens
<220> FEATURE:
<221> NAME/KEY: misc_feature
<223> OTHER INFORMATION: Incyte Clone No: 4624811T6

<400> SEQUENCE: 16

```
aaatgtctcc actcaagttg tccttgaaaa aaatttagaa gcagcaacaa tcatcttggt      60
tagttacaag cagtctagtg caatttataa aatcgagcaa aatttggatg tgtgtcttat      120
ccctctgtag acacgggacc ctttttttgag gtctcttttct ttagggtctg gtagcatcat    180
gactgggaca ctttccaaag ccttcttcct ttggactcta tgtaaaataa ttctatagac      240
ccctgtgatt gagctgcgag catctctccc ttggttatttt cgaatatgct cttctgtaat    300
gcccaaatgt tctaaagtgc ttttgacctc attttcttct tccttgagag tgctggtttc     360
cgacaaatgt ttgggatcca gttggaaagg ttccaaaggt gtagggtatg gcacccttg      420 cat                                                                    423
```

<210> SEQ ID NO 17
<211> LENGTH: 564
<212> TYPE: DNA
<213> ORGANISM: Homo sapiens
<220> FEATURE:
<221> NAME/KEY: misc_feature
<223> OTHER INFORMATION: Incyte Clone No: 6559834H1

<400> SEQUENCE: 17

```
attgaggccg cgggaatcca aagggaaac aaacgaaacc agatgaaaaa aagtgattcc       60
```

-continued

```
aagtcaagat tcaaatgga atctaagaa aaggtggcca ttaagatcct ggacaagacc      120
aagttagacc agaaaaccca gaggctacta tcccgagaaa tctccagcat ggaaaagctg    180
caccatccca acatcatccg cctttacgaa gtggtgagaa ccctatccaa gctgcacttg    240
gtgatggagt atgcaggggg tggggagctc ttcggaaaaa ttagcactga ggggaagctc    300
tctgaaccag aaagcaagct catcttctcc cagattgtgt ctgccgtgaa gcacatgcat    360
gaaaaccaaa ttattcatag agatctgaaa gcagaaaatg tattctatac cagtaatact    420
tgtgtgaagg tgggcgattt tggattcagc acagtaagca aaaaggtgaa atgctgaac     480 actttctgtg gtctcctcc ctacgctgcg cctgaactct ccgggacga gcactacatc     540 ggcatttacg tggatatctg ggcc                                           564
```

<210> SEQ ID NO 18
<211> LENGTH: 598
<212> TYPE: DNA
<213> ORGANISM: Homo sapiens
<220> FEATURE:
<221> NAME/KEY: misc_feature
<223> OTHER INFORMATION: Incyte Clone No: 670279F1
<220> FEATURE:
<221> NAME/KEY: unsure
<222> LOCATION: 227
<223> OTHER INFORMATION: a, t, c, g, or other

<400> SEQUENCE: 18

```
gcatatctca aatttaagtt tatttaaaaa ttacaaaaat gtctccactc aagttgtcct     60
tgaaaaaaat ttagaagcag caacaatcat cttggttagt tacaagcagt ctagtgcaat   120
ttataaaatc gagcaaaatt tggatgtgtg tcttatccct ctgtagacac gggacccttt   180
tttgaggtct ctttctttag ggtctggtag catcatgact gggacanttt ccaaagcctt   240
cttcctttgg actctatgta aaataattct atagacccct gtgattgagc tgcgagcatc   300
tctcccttgg ttatttcgaa tatgctcttc tgtaatgccc aaatgttcta aagtgctttt   360
gacctcattt tcttcttcct tgagagtgct ggtttccgac aaatgtttgg gatccagttg   420
gaaaggttcc aaaggtgtag ggtatggcac cccttgcatc cattcatcat tcatgatgca   480
gtcgattccg tacctctccg tggggatctg ctgaaggact cctcggatga gtcggtggca   540
gggctctgac acgtgcggcg gtacactgta tgtgccctcg aggatgctct tttttagt     598
```

<210> SEQ ID NO 19
<211> LENGTH: 288
<212> TYPE: DNA
<213> ORGANISM: Homo sapiens
<220> FEATURE:
<221> NAME/KEY: misc_feature
<223> OTHER INFORMATION: Incyte Clone No: 670279H1
<220> FEATURE:
<221> NAME/KEY: unsure
<222> LOCATION: 19, 153, 268
<223> OTHER INFORMATION: a, t, c, g, or other

<400> SEQUENCE: 19

```
gctgcaccat cccaacatna tccgccttta cgaagtggtg gagaccctat ccaagctgca    60
cttggtgatg gagtatgcag ggggtgggga gctcttcgga aaaattagca ctgaggggaa   120
gctctctgaa ccagaaagca agctcatctt ctnccagatt gtgtctgccg tgaagcacat   180
gcatgaaaac caaattattc atagagatct gaaagcagaa aatgtattct ataccagtaa   240
tacttgtgtg aaggtgggcg attttggntt cagcacagta agcaaaaa                288
```

```
<210> SEQ ID NO 20
<211> LENGTH: 546
<212> TYPE: DNA
<213> ORGANISM: Homo sapiens
<220> FEATURE:
<221> NAME/KEY: misc_feature
<223> OTHER INFORMATION: Incyte Clone No: 670279R1
<220> FEATURE:
<221> NAME/KEY: unsure
<222> LOCATION: 534
<223> OTHER INFORMATION: a, t, c, g, or other

<400> SEQUENCE: 20
gctgcaccat cccaacatca tccgccttta cgagtggtgg agaccctatc caagctgcac      60
ttggtgatgg agtatgcagg gggtggggag ctcttcggaa aaattagcac tgaggggaag     120
ctctctgaac cagaaagcaa gctcatcttc tcccagattg tgtctgccgt gaagcacatg     180
catgaaaacc aaattattca tagagatctg aaagcagaaa atgtattcta taccagtaat     240
acttgtgtga aggtgggcga ttttggattc agcacagtaa gcaaaaaagg tgaaatgctg     300
aacactttct gtgggtctcc tccctacgct gcgcctgaac tcttccggga cgagcactac     360
atcggcattt acgtggatat ctgggccttg ggggtgcttt tgtacttcat ggtgactggc     420
accatgccat ttcgggcaga aaccgtggcc aaactaaaaa agagcatcct cgagggcaca     480
tacagtgtac cgccgcacgt gtcagagccc tgccaccgac tcatccgagg agtncttcag     540
cagatc                                                                546

<210> SEQ ID NO 21
<211> LENGTH: 383
<212> TYPE: DNA
<213> ORGANISM: Homo sapiens
<220> FEATURE:
<221> NAME/KEY: misc_feature
<223> OTHER INFORMATION: Incyte Clone No: 670279R6
<220> FEATURE:
<221> NAME/KEY: unsure
<222> LOCATION: 81, 147
<223> OTHER INFORMATION: a, t, c, g, or other

<400> SEQUENCE: 21
gctgcaccat cccaacatca tccgccttta cgaatggtgg agaccctatc caagctgcac      60
ttggtgatgg agtatgcagg nggtggggag ctcttcggaa aaattagcac tgaggggaag     120
ctctctgaac cagaaagcaa gctcatnttc tcccagattg tgtctgccgt gaagcacatg     180
catgaaaacc aaattattca tagagatctg aaagcagaaa atgtattcta taccagtaat     240
acttgtgtga aggtgggcga ttttggattc agcacagtaa gcaaaaaagg tgaaatgctg     300
aacactttct gtgggtctcc tccctacgct gcgcctgaac tcttccggga cgagcactac     360
atcgggcatt tacgtgggat atc                                             383

<210> SEQ ID NO 22
<211> LENGTH: 537
<212> TYPE: DNA
<213> ORGANISM: Homo sapiens
<220> FEATURE:
<221> NAME/KEY: misc_feature
<223> OTHER INFORMATION: Incyte Clone No: 670279T6
<220> FEATURE:
<221> NAME/KEY: unsure
<222> LOCATION: 504
<223> OTHER INFORMATION: a, t, c, g, or other

<400> SEQUENCE: 22
aatgtctcca ctcaagttgt ccttgaaaaa aatttagaag cagcaacaat catcttggtt      60
```

-continued

```
agttacaagc agtctagtgc aatttataaa atcgagcaaa atttggatgt gtgtcttatc    120
cctctgtaga cacgggaccc ttttttgagg tctctttctt tagggtctgg tagcatcatg    180
actgggacac tttccaaagc cttcttcctt tggactctat gtaaataat tctatagacc    240 cctgtgattg agctgcgagc atctctccct tggttatttc gaatatgctc ttctgtaatg    300
cccaaatgtt ctaaagtgct tttgacctca ttttcttctt ccttgagagt gctggtttcc    360
gacaaatgtt tgggatccag ttggaaaggt tccaaggtg tagggtatgg caccccttgc     420
atccattcat cattcatgat gcagtcgatt ccgtacctct ccgtgggat ctgctgaagg     480 actcctcgga tgagtcggtg gcanggcctg acacgtgcgg cggtacactg tatgtgc      537
```

<210> SEQ ID NO 23
<211> LENGTH: 279
<212> TYPE: DNA
<213> ORGANISM: Homo sapiens
<220> FEATURE:
<221> NAME/KEY: misc_feature
<223> OTHER INFORMATION: Incyte Clone No: 4936446H1
<220> FEATURE:
<221> NAME/KEY: unsure
<222> LOCATION: 84
<223> OTHER INFORMATION: a, t, c, g, or other

<400> SEQUENCE: 23

```
gcatcatgaa tgatgaatgg atgcaagggg tgccataccc tacacctttg gaacctttcc    60
aactggatcc caaacatttg tcgnaaacca gcactctcaa ggaagaagaa aatgaggtca   120
aaagcacttt agaacatttg gcattacag aagagcatat tcgaaataac caagggagag    180
atgctcgcag ctcaatcaca ggggtctata gaattatttt acatagagtc caaggaaga    240 aggctttgga aagtgtccca gtcatgatgc taccagacc                          279
```

<210> SEQ ID NO 24
<211> LENGTH: 488
<212> TYPE: DNA
<213> ORGANISM: Rattus norvegicus
<220> FEATURE:
<221> NAME/KEY: misc_feature
<223> OTHER INFORMATION: Incyte Template No: 216150.1

<400> SEQUENCE: 24

```
aaaagttgca ccatcccaac attgtccgtc tttatgaagt cgtggagacc ctgtccaagc    60
tccacctagt gatggagtat gcaggaggtg gggagctctt tgggaaaatt agcaccgagg   120
ggaaactttc tgaaccggaa agcaagctca tcttctccca gatcgtgtct gccgtgaagc   180
aacggcatga gaaccaaatt atccacagag atctgaaagc agaaaacgtc ttctatacca   240
gtagcacttg tgtgaaggtg ggggattttg gattcagcac cgtaagtaag aaaggtgaga   300
tgctgaacac cttctgtggg tctccgccct acgctgcacc ggaactcttc cgtgacgagc    360
actatgttgg cgtttatgtg gatatctggg ccttgggtgt ccttttgtac ttcatggtga    420
ctggtacgat gccatttcga gcagaaaccg tggccaaact gaaaaagagc atcctcgatg    480
gtgcctac                                                             488
```

<210> SEQ ID NO 25
<211> LENGTH: 272
<212> TYPE: DNA
<213> ORGANISM: Rattus norvegicus
<220> FEATURE:
<221> NAME/KEY: misc_feature
<223> OTHER INFORMATION: Incyte Clone No: 701925441H1

```
<400> SEQUENCE: 25
agccgcgcca gctgacacct ttcgagaaac tgactcagga catgtgccaa gatgagaagg      60
tggtgaggga gatcacgctg gggaaacgca taggcttcta tcgaattcga ggggagatcg     120
gaagcggaaa cttttcccag gtcaagctgg gaattcactc cctaaccaaa gaaaaggtgg     180
ccattaagat tctggacaaa accaagttag accagaaaac ccaaaggctg ttatccagag     240
aaatttccag cagccggaaa tgcaccatcc ca                                    272

<210> SEQ ID NO 26
<211> LENGTH: 303
<212> TYPE: DNA
<213> ORGANISM: Rattus norvegicus
<220> FEATURE:
<221> NAME/KEY: misc_feature
<223> OTHER INFORMATION: Incyte Clone No: 701910632H1
<220> FEATURE:
<221> NAME/KEY: unsure
<222> LOCATION: 183, 190, 287, 291
<223> OTHER INFORMATION: a, t, c, g, or other

<400> SEQUENCE: 26
aagttgcacc atcccaacat tgtccgtctt tatgaagtcg tggagaccct gtccaagctc      60
cacctagtga tggagtatgc aggaggtggg gagctctttg ggaaaattag caccgagggg     120
aaactttctg aaccggaaag caagctcatc ttctcccaga tcgtgtctgc cgtgaagcaa     180
atnccatgan aaccaaatta tccacagaga tctgaaagca gaaaacgtct tctataccag     240
tagcacttgt gtgaaggtgg gggatttttgg attcagcacc gtaagtnaga naggtgagat     300
gct                                                                    303

<210> SEQ ID NO 27
<211> LENGTH: 299
<212> TYPE: DNA
<213> ORGANISM: Rattus norvegicus
<220> FEATURE:
<221> NAME/KEY: misc_feature
<223> OTHER INFORMATION: Incyte Clone No: 701905514H1
<220> FEATURE:
<221> NAME/KEY: unsure
<222> LOCATION: 3, 29
<223> OTHER INFORMATION: a, t, c, g, or other

<400> SEQUENCE: 27
ganaaccaaa ttatccacag agatctgana gcagaaaacg tcttctatac cagtagcact      60
tgtgtgaagg tgggggattt tggattcagc accgtaagta agaaaggtga gatgctgaac     120
accttctgtg ggtctccgcc ctacgctgca ccggaactct ccgtgacga gcactatgtt      180 ggcgtttatg tggatatctg ggcctgggtg tccttttgta cttcatggtg actggtacga     240
tgccattcga gcagaaaccg tggccaaact gaaaagagc atcctcgagg gtgcctaca       299

<210> SEQ ID NO 28
<211> LENGTH: 258
<212> TYPE: DNA
<213> ORGANISM: Rattus norvegicus
<220> FEATURE:
<221> NAME/KEY: misc_feature
<223> OTHER INFORMATION: Incyte Clone No: 701293826H1

<400> SEQUENCE: 28
aatggatgcg aggggtgccg taccctccc ctctggaacc tttccaactg gatcctaaac       60
atttgtcgga aactagcacc ctcaaagaag aagaaaacga ggtgaaaagc actttagagc     120
```

```
acttggggat cacagacgaa catatccgga ataaccaagg gagagacgct cgaagctcta    180 tcacggggt ctatagaatc attttacatc gagtgcaaag aagaaaagcc tggaaagtgt    240
gccaatggcg acactacc                                                  258
```

<210> SEQ ID NO 29
<211> LENGTH: 113
<212> TYPE: DNA
<213> ORGANISM: Rattus norvegicus
<220> FEATURE:
<221> NAME/KEY: misc_feature
<223> OTHER INFORMATION: Incyte Clone No: 700949543H1
<220> FEATURE:
<221> NAME/KEY: unsure
<222> LOCATION: 60, 102, 106
<223> OTHER INFORMATION: a, t, c, g, or other

<400> SEQUENCE: 29

```
tacctggcag gcgtaccagc tttccctata agtggagtcg tattaggagc ttgggcgtan     60
atccatgggt ccataggctg ttttcctgtg tggaaattgt tnatcncgct cca           113
```

<210> SEQ ID NO 30
<211> LENGTH: 300
<212> TYPE: DNA
<213> ORGANISM: Macaca fascicularis
<220> FEATURE:
<221> NAME/KEY: misc_feature
<223> OTHER INFORMATION: Incyte Clone No: 700706950H1
<220> FEATURE:
<221> NAME/KEY: unsure
<222> LOCATION: 191, 227, 247-248, 252, 255-256, 269, 285, 287, 290,
      293, 296
<223> OTHER INFORMATION: a, t, c, g, or other

<400> SEQUENCE: 30

```
gaagtcgtgg agaccctatc taagctgcac ttggtgatgg aatatgcagg gggtggggag     60
ctgttcggaa aaattagcac tgaggggaag ctctctgaac cagaaagcaa gctcatcttc    120
tcccagattg tgtctgccgt gaagcactgc atgaaaccaa ttattcacga gtctgaagca    180
gaaatgtatc natacagtat actgtgtgaa gtggcgattt ggatcancag taattaaaaa    240
gtgaatnnaa cnttnngtgg ctctccatnt gacgaccttc ggcgncntan cgnatncgtg    300
```

<210> SEQ ID NO 31
<211> LENGTH: 334
<212> TYPE: PRT
<213> ORGANISM: Caenorhabditis elegans
<220> FEATURE:
<221> NAME/KEY: misc_feature
<223> OTHER INFORMATION: GenBank Accession No: g3877329

<400> SEQUENCE: 31

```
Met Ser Glu Lys Thr Gln Tyr Glu Arg Ala Ile Leu Gln Leu Asn
  1               5                  10                  15

Asn Asp Pro Val Val His Lys Glu Val Trp Ala Cys Ile Val Ser
                 20                  25                  30

Tyr Gly Lys Arg Lys Leu Trp Phe Gln Val Ala Leu Gly Arg Arg
                 35                  40                  45

Ile Gly Phe Tyr Arg Leu Gly Lys Glu Leu Gly Ala Gly Asn Phe
                 50                  55                  60

Ser Lys Val Lys Leu Gly Val His Gln Leu Thr Lys Glu Lys Val
                 65                  70                  75

Ala Val Lys Ile Met Asp Lys Ala Lys Met Asp Ala Lys Ala Gln
```

```
                    80                  85                  90
Lys Leu Leu Ser Arg Glu Ile Gln Ala Met Glu Glu Met Asn His
                    95                 100                 105
Pro Asn Ile Val Lys Leu Phe Glu Val Val Glu Thr Leu Thr Arg
                   110                 115                 120
Val His Leu Val Ile Glu Tyr Ala Ser Gly Gly Glu Leu Tyr Thr
                   125                 130                 135
Tyr Val His Glu Arg Gly Lys Leu Thr Glu Gly Asp Ala Lys Pro
                   140                 145                 150
Leu Phe Ala Gln Ile Val Ser Ala Val Ser His Met His Ser Arg
                   155                 160                 165
Asn Ile Val His Arg Asp Ile Lys Ala Glu Asn Val Met Phe Ser
                   170                 175                 180
Ser Pro Asn Thr Val Lys Leu Val Asp Phe Gly Phe Ser Cys Leu
                   185                 190                 195
Val Asp Arg Glu Gln Met Leu Arg Thr Phe Cys Gly Ser Pro Pro
                   200                 205                 210
Tyr Ala Ala Pro Glu Leu Phe Gln Asp Thr Ser Tyr Ala Gly Glu
                   215                 220                 225
Leu Val Asp Val Trp Ala Leu Gly Val Leu Leu Phe Phe Met Leu
                   230                 235                 240
Ile Gly Val Thr Pro Phe Lys Ala Glu Thr Val Pro Asp Met Lys
                   245                 250                 255
Val Leu Ile Thr Ala Gly Lys Tyr Gln Ile Pro Asp Tyr Val Ser
                   260                 265                 270
Leu Leu Ala Thr Glu Leu Ile Lys Ser Met Leu Lys Thr Asp Thr
                   275                 280                 285
Gly Gln Arg Ala Asp Ile Asp Ser Val Lys Lys His Phe Trp Met
                   290                 295                 300
Arg Asp Cys Arg Phe Thr Lys Ser Tyr Leu Ser Ile Lys Ala Thr
                   305                 310                 315
Ala Lys Ile Asp Asn Glu Glu Glu Lys Lys Ala Ile Asp Asp Lys
                   320                 325                 330
Val Ile Phe Val

<210> SEQ ID NO 32
<211> LENGTH: 793
<212> TYPE: PRT
<213> ORGANISM: Rattus norvegicus
<220> FEATURE:
<221> NAME/KEY: misc_feature
<223> OTHER INFORMATION: GenBank Accession No: g2052189

<400> SEQUENCE: 32

Met Ser Ala Arg Thr Pro Leu Pro Thr Val Asn Glu Arg Asp Thr
  1               5                  10                  15
Glu Asn His Thr Ser Val Asp Gly Tyr Thr Glu Thr His Ile Pro
                   20                  25                  30
Pro Thr Lys Ser Ser Ser Arg Gln Asn Ile Pro Arg Cys Arg Asn
                   35                  40                  45
Ser Ile Thr Ser Ala Thr Asp Glu Gln Pro His Ile Gly Asn Tyr
                   50                  55                  60
Arg Leu Gln Lys Thr Ile Gly Lys Gly Asn Phe Ala Lys Val Lys
                   65                  70                  75
Leu Ala Arg His Val Leu Thr Gly Arg Glu Val Ala Val Lys Ile
```

-continued

```
                80                  85                  90
Ile Asp Lys Thr Gln Leu Asn Pro Thr Ser Leu Gln Lys Leu Phe
                    95                 100                 105
Arg Glu Val Arg Ile Met Lys Ile Leu Asn His Pro Asn Ile Val
                   110                 115                 120
Lys Leu Phe Glu Val Ile Glu Thr Glu Lys Thr Leu Tyr Leu Val
                   125                 130                 135
Met Glu Tyr Ala Ser Gly Gly Glu Val Phe Asp Tyr Leu Val Ala
                   140                 145                 150
His Gly Arg Met Lys Glu Lys Glu Ala Arg Ala Lys Phe Arg Gln
                   155                 160                 165
Ile Val Ser Ala Val Gln Tyr Cys His Gln Lys Cys Ile Val His
                   170                 175                 180
Arg Asp Leu Lys Ala Glu Asn Leu Leu Leu Asp Ala Asp Met Asn
                   185                 190                 195
Ile Lys Ile Ala Asp Phe Gly Phe Ser Asn Glu Phe Thr Val Gly
                   200                 205                 210
Asn Lys Leu Asp Thr Phe Cys Gly Ser Pro Pro Tyr Ala Ala Pro
                   215                 220                 225
Glu Leu Phe Gln Gly Lys Lys Tyr Asp Gly Pro Glu Val Asp Val
                   230                 235                 240
Trp Ser Leu Gly Val Ile Leu Tyr Thr Leu Val Ser Gly Ser Leu
                   245                 250                 255
Pro Phe Asp Gly Gln Asn Leu Lys Glu Leu Arg Glu Arg Val Leu
                   260                 265                 270
Arg Gly Lys Tyr Arg Val Pro Phe Tyr Met Ser Thr Asp Cys Glu
                   275                 280                 285
Asn Leu Leu Lys Lys Leu Leu Val Leu Asn Pro Ile Lys Arg Gly
                   290                 295                 300
Ser Leu Glu Gln Ile Met Lys Asp Arg Trp Met Asn Val Gly His
                   305                 310                 315
Glu Glu Glu Glu Leu Lys Pro Tyr Ser Glu Pro Glu Leu Asp Leu
                   320                 325                 330
Asn Asp Ala Lys Arg Ile Asp Ile Met Val Thr Met Gly Phe Ala
                   335                 340                 345
Arg Asp Glu Ile Asn Asp Ala Leu Val Ser Gln Lys Tyr Asp Glu
                   350                 355                 360
Val Met Ala Thr Tyr Ile Leu Leu Gly Arg Lys Pro Pro Glu Phe
                   365                 370                 375
Glu Gly Gly Glu Ser Leu Ser Ser Gly Asn Leu Cys Gln Arg Ser
                   380                 385                 390
Arg Pro Ser Ser Asp Leu Asn Asn Ser Thr Leu Gln Ser Pro Ala
                   395                 400                 405
His Leu Lys Val Gln Arg Ser Ile Ser Ala Asn Gln Lys Gln Arg
                   410                 415                 420
Arg Phe Ser Asp His Ala Gly Pro Ser Ile Pro Pro Ala Val Ser
                   425                 430                 435
Tyr Thr Lys Arg Pro Gln Ala Asn Ser Val Glu Ser Glu Gln Lys
                   440                 445                 450
Glu Glu Trp Asp Lys Asp Thr Ala Arg Arg Leu Gly Ser Thr Thr
                   455                 460                 465
Val Gly Ser Lys Ser Glu Val Thr Ala Ser Pro Leu Val Gly Pro
                   470                 475                 480
```

```
Asp Arg Lys Lys Ser Ser Ala Gly Pro Ser Asn Asn Val Tyr Ser
                485                 490                 495

Gly Gly Ser Met Thr Arg Arg Asn Thr Tyr Val Cys Glu Arg Ser
                500                 505                 510

Thr Asp Arg Tyr Ala Ala Leu Gln Asn Gly Arg Asp Ser Ser Leu
                515                 520                 525

Thr Glu Met Ser Ala Ser Ser Met Ser Ser Thr Gly Ser Thr Val
                530                 535                 540

Ala Ser Ala Gly Pro Ser Ala Arg Pro Arg His Gln Lys Ser Met
                545                 550                 555

Ser Thr Ser Gly His Pro Ile Lys Val Thr Leu Pro Thr Ile Lys
                560                 565                 570

Asp Gly Ser Glu Ala Tyr Arg Pro Gly Thr Ala Gln Arg Val Pro
                575                 580                 585

Ala Ala Ser Pro Ser Ala His Ser Ile Ser Ala Ser Thr Pro Asp
                590                 595                 600

Arg Thr Arg Phe Pro Arg Gly Ser Ser Ser Arg Ser Thr Phe His
                605                 610                 615

Gly Glu Gln Leu Arg Glu Arg Ser Ala Ala Tyr Ser Gly Pro
                620                 625                 630

Pro Ala Ser Pro Ser His Asp Thr Ala Ala Leu Ala His Ala Arg
                635                 640                 645

Arg Gly Thr Ser Thr Gly Ile Ile Ser Lys Ile Thr Ser Lys Phe
                650                 655                 660

Val Arg Arg Asp Pro Ser Glu Gly Ala Ser Gly Arg Thr Asp
                665                 670                 675

Thr Ala Arg Gly Ser Ser Gly Glu Pro Lys Asp Lys Glu Gly Gly
                680                 685                 690

Lys Glu Ala Lys Pro Arg Ser Leu Arg Phe Thr Trp Ser Met Lys
                695                 700                 705

Thr Thr Ser Ser Met Asp Pro Asn Asp Met Val Arg Glu Ile Arg
                710                 715                 720

Lys Val Leu Asp Ala Asn Thr Cys Asp Tyr Glu Gln Arg Glu Arg
                725                 730                 735

Phe Leu Leu Phe Cys Val His Gly Asp Ala Arg Gln Asp Ser Leu
                740                 745                 750

Val Gln Trp Glu Met Glu Val Cys Lys Leu Pro Arg Leu Ser Leu
                755                 760                 765

Asn Gly Val Arg Phe Lys Arg Ile Ser Gly Thr Ser Ile Ala Phe
                770                 775                 780

Lys Asn Ile Ala Ser Lys Ile Ala Asn Glu Leu Lys Leu
                785                 790

<210> SEQ ID NO 33
<211> LENGTH: 729
<212> TYPE: PRT
<213> ORGANISM: Homo sapiens
<220> FEATURE:
<221> NAME/KEY: misc_feature
<223> OTHER INFORMATION: GenBank Accession No: g3089349

<400> SEQUENCE: 33

Met Ser Thr Arg Thr Pro Leu Pro Thr Val Asn Glu Arg Asp Thr
 1               5                  10                  15

Glu Asn His Thr Ser His Gly Asp Gly Arg Gln Glu Val Thr Ser
```

```
                     20                  25                  30
Arg Thr Ser Arg Ser Gly Ala Arg Cys Arg Asn Ser Ile Ala Ser
                 35                  40                  45
Cys Ala Asp Glu Gln Pro His Ile Gly Asn Tyr Arg Leu Leu Lys
             50                  55                  60
Thr Ile Gly Lys Gly Asn Phe Ala Lys Val Lys Leu Ala Arg His
         65                  70                  75
Ile Leu Thr Gly Arg Glu Val Ala Ile Lys Ile Asp Lys Thr
     80                  85                  90
Gln Leu Asn Pro Thr Ser Leu Gln Lys Leu Phe Arg Glu Val Arg
                 95                 100                 105
Ile Met Lys Ile Leu Asn His Pro Asn Ile Val Lys Leu Phe Glu
            110                 115                 120
Val Ile Glu Thr Glu Lys Thr Leu Tyr Leu Ile Met Glu Tyr Ala
            125                 130                 135
Ser Gly Gly Glu Val Phe Asp Tyr Leu Val Ala His Gly Arg Met
            140                 145                 150
Lys Glu Lys Glu Ala Arg Ser Lys Phe Arg Gln Ile Val Ser Ala
            155                 160                 165
Val Gln Tyr Cys His Gln Lys Arg Ile Val His Arg Asp Leu Lys
            170                 175                 180
Ala Glu Asn Leu Leu Leu Asp Ala Asp Met Asn Ile Lys Ile Ala
            185                 190                 195
Asp Phe Gly Phe Ser Asn Glu Phe Thr Val Gly Gly Lys Leu Asp
            200                 205                 210
Thr Phe Cys Gly Ser Pro Pro Tyr Ala Ala Pro Glu Leu Phe Gln
            215                 220                 225
Gly Lys Lys Tyr Asp Gly Pro Glu Val Asp Val Trp Ser Leu Gly
            230                 235                 240
Val Ile Leu Tyr Thr Leu Val Ser Gly Ser Leu Pro Phe Asp Gly
            245                 250                 255
Gln Asn Leu Lys Glu Leu Arg Glu Arg Val Leu Arg Gly Lys Tyr
            260                 265                 270
Arg Ile Pro Phe Tyr Met Ser Thr Asp Cys Glu Asn Leu Leu Lys
            275                 280                 285
Arg Phe Leu Val Leu Asn Pro Ile Lys Arg Gly Thr Leu Glu Gln
            290                 295                 300
Ile Met Lys Asp Arg Trp Ile Asn Ala Gly His Glu Glu Asp Glu
            305                 310                 315
Leu Lys Pro Phe Val Glu Pro Glu Leu Asp Ile Ser Asp Gln Lys
            320                 325                 330
Arg Ile Asp Ile Met Val Gly Met Gly Tyr Ser Gln Glu Glu Ile
            335                 340                 345
Gln Glu Ser Leu Ser Lys Met Lys Tyr Asp Glu Ile Thr Ala Thr
            350                 355                 360
Tyr Leu Leu Leu Gly Arg Lys Ser Ser Glu Leu Asp Ala Ser Asp
            365                 370                 375
Ser Ser Ser Ser Ser Asn Leu Ser Leu Ala Lys Val Arg Pro Ser
            380                 385                 390
Ser Asp Leu Asn Asn Ser Thr Gly Gln Ser Pro His His Lys Val
            395                 400                 405
Gln Arg Ser Val Ser Ser Ser Gln Lys Gln Arg Arg Tyr Ser Asp
            410                 415                 420
```

```
His Ala Gly Pro Ala Ile Pro Ser Val Val Ala Tyr Pro Lys Arg
                425                 430                 435

Ser Gln Thr Ser Thr Ala Asp Gly Asp Leu Lys Glu Asp Gly Ile
                440                 445                 450

Ser Ser Arg Lys Ser Ser Gly Ser Ala Val Gly Gly Lys Gly Ile
                455                 460                 465

Ala Pro Ala Ser Pro Met Leu Gly Asn Ala Ser Asn Pro Asn Lys
                470                 475                 480

Ala Asp Ile Pro Glu Arg Lys Lys Ser Ser Thr Val Pro Ser Ser
                485                 490                 495

Asn Thr Ala Ser Gly Gly Met Thr Arg Arg Asn Thr Tyr Val Cys
                500                 505                 510

Ser Glu Arg Thr Thr Ala Asp Arg His Ser Val Ile Gln Asn Gly
                515                 520                 525

Lys Glu Asn Ser Thr Ile Pro Asp Gln Arg Thr Pro Val Ala Ser
                530                 535                 540

Thr His Ser Ile Ser Ser Ala Ala Thr Pro Asp Arg Ile Arg Phe
                545                 550                 555

Pro Arg Gly Thr Ala Ser Arg Ser Thr Phe His Gly Gln Pro Arg
                560                 565                 570

Glu Arg Arg Thr Ala Thr Tyr Asn Gly Pro Pro Ala Ser Pro Ser
                575                 580                 585

Leu Ser His Glu Ala Thr Pro Leu Ser Gln Thr Arg Ser Arg Gly
                590                 595                 600

Ser Thr Asn Leu Phe Ser Lys Leu Thr Ser Lys Leu Thr Arg Ser
                605                 610                 615

Arg Asn Val Ser Ala Glu Gln Lys Asp Glu Asn Lys Glu Ala Lys
                620                 625                 630

Pro Arg Ser Leu Arg Phe Thr Trp Ser Met Lys Thr Thr Ser Ser
                635                 640                 645

Met Asp Pro Gly Asp Met Met Arg Glu Ile Arg Lys Val Leu Asp
                650                 655                 660

Ala Asn Asn Cys Asp Tyr Glu Gln Arg Glu Arg Phe Leu Leu Phe
                665                 670                 675

Cys Val His Gly Asp Gly His Ala Glu Asn Leu Val Gln Trp Glu
                680                 685                 690

Met Glu Val Cys Lys Leu Pro Arg Leu Ser Leu Asn Gly Val Arg
                695                 700                 705

Phe Lys Arg Ile Ser Gly Thr Ser Ile Ala Phe Lys Asn Ile Ala
                710                 715                 720

Ser Lys Ile Ala Asn Glu Leu Lys Leu
                725

<210> SEQ ID NO 34
<211> LENGTH: 776
<212> TYPE: PRT
<213> ORGANISM: Rattus norvegicus
<220> FEATURE:
<221> NAME/KEY: misc_feature
<223> OTHER INFORMATION: GenBank Accession No: g5672676

<400> SEQUENCE: 34

Met Val Ile Met Ser Glu Phe Ser Ala Val Pro Thr Gly Thr Gly
  1               5                  10                  15

Gln Gly Gln Gln Lys Pro Leu Arg Val Gly Phe Tyr Asp Val Glu
```

```
                         20                  25                  30
Arg Thr Leu Gly Lys Gly Asn Phe Ala Val Lys Leu Ala Arg
                 35                  40                  45
His Arg Val Thr Lys Thr Gln Val Ala Ile Lys Ile Asp Lys
                 50                  55                  60
Thr Arg Leu Asp Ser Ser Asn Leu Glu Lys Ile Tyr Arg Glu Val
                 65                  70                  75
Gln Leu Met Lys Leu Leu Asn His Pro Asn Ile Ile Lys Leu Tyr
                 80                  85                  90
Gln Val Met Glu Thr Lys Asp Met Leu Tyr Ile Val Thr Glu Phe
                 95                 100                 105
Ala Lys Asn Gly Glu Met Phe Asp Tyr Leu Thr Ser Asn Gly His
                110                 115                 120
Leu Ser Glu Asn Glu Ala Arg Lys Lys Phe Trp Gln Ile Leu Ser
                125                 130                 135
Ala Val Glu Tyr Cys His Asn His His Ile Val His Arg Asp Leu
                140                 145                 150
Lys Thr Glu Asn Leu Leu Leu Asp Gly Asn Met Asp Ile Lys Leu
                155                 160                 165
Ala Asp Phe Gly Phe Gly Asn Phe Tyr Lys Pro Gly Glu Pro Leu
                170                 175                 180
Ser Thr Trp Cys Gly Ser Pro Pro Tyr Ala Ala Pro Glu Val Phe
                185                 190                 195
Glu Gly Lys Glu Tyr Glu Gly Pro Gln Leu Asp Ile Trp Ser Leu
                200                 205                 210
Gly Val Val Leu Tyr Val Leu Val Cys Gly Ser Leu Pro Phe Asp
                215                 220                 225
Gly Pro Asn Leu Pro Thr Leu Arg Gln Arg Val Leu Glu Gly Arg
                230                 235                 240
Phe Arg Ile Pro Phe Phe Met Ser Gln Asp Cys Glu Thr Leu Ile
                245                 250                 255
Arg Arg Met Leu Val Val Asp Pro Ala Lys Arg Ile Thr Ile Ala
                260                 265                 270
Gln Ile Arg Gln His Arg Trp Met Gln Ala Asp Pro Thr Leu Leu
                275                 280                 285
Gln Gln Asp Asp Pro Ala Phe Ser Met Gln Gly Tyr Thr Ser Asn
                290                 295                 300
Leu Gly Asp Tyr Asn Glu Gln Val Leu Gly Ile Met Gln Ala Leu
                305                 310                 315
Gly Ile Asp Arg Gln Arg Thr Val Glu Ser Leu Gln Asn Ser Ser
                320                 325                 330
Tyr Asn His Phe Ala Ala Ile Tyr Tyr Leu Leu Leu Glu Arg Leu
                335                 340                 345
Arg Glu His Arg Ser Thr Gln Pro Ser Ser Arg Ala Thr Pro Ala
                350                 355                 360
Pro Ala Arg Gln Pro Gln Leu Arg Asn Ser Asp Leu Ser Ser Leu
                365                 370                 375
Glu Val Pro Gln Glu Ile Leu Pro Cys Asp Pro Phe Arg Pro Ser
                380                 385                 390
Leu Leu Cys Pro Gln Pro Gln Ala Leu Ala Gln Ser Val Leu Gln
                395                 400                 405
Ala Glu Ile Asp Cys Asp Leu His Ser Ser Leu Gln Pro Leu Phe
                410                 415                 420
```

```
                    -continued

Phe Pro Leu Asp Thr Asn Cys Ser Gly Val Phe Arg His Arg Ser
                425                 430                 435

Ile Ser Pro Ser Ser Leu Leu Asp Thr Ala Ile Ser Glu Glu Ala
                440                 445                 450

Arg Gln Gly Pro Ser Leu Glu Glu Gln Glu Val Gln Glu Pro
                455                 460                 465

Leu Pro Gly Ser Thr Gly Arg Arg His Thr Leu Ala Glu Val Ser
                470                 475                 480

Thr His Phe Ser Pro Leu Asn Pro Pro Cys Ile Ile Val Ser Ser
                485                 490                 495

Ser Ala Ala Val Ser Pro Ser Glu Gly Thr Ser Ser Asp Ser Cys
                500                 505                 510

Leu Pro Phe Ser Ala Ser Glu Gly Pro Ala Gly Leu Gly Gly Gly
                515                 520                 525

Leu Ala Thr Pro Gly Leu Leu Gly Thr Ser Ser Pro Val Arg Leu
                530                 535                 540

Ala Ser Pro Phe Leu Gly Ser Gln Ser Ala Thr Pro Val Leu Gln
                545                 550                 555

Ser Gln Ala Gly Leu Gly Ala Thr Val Leu Pro Pro Val Ser Phe
                560                 565                 570

Gln Glu Gly Arg Arg Ala Ser Asp Thr Ser Leu Thr Gln Gly Leu
                575                 580                 585

Lys Ala Phe Arg Gln Gln Leu Arg Lys Asn Ala Arg Thr Lys Gly
                590                 595                 600

Phe Leu Gly Leu Asn Lys Ile Lys Gly Leu Ala Arg Gln Val Cys
                605                 610                 615

Gln Ser Ser Ile Arg Gly Ser Arg Gly Gly Met Ser Thr Phe His
                620                 625                 630

Thr Pro Ala Pro Ser Ser Gly Leu Gln Gly Cys Thr Ala Ser Ser
                635                 640                 645

Arg Glu Gly Arg Ser Leu Leu Glu Glu Val Leu His Gln Gln Arg
                650                 655                 660

Leu Leu Gln Leu Gln His His Ser Ala Val Ser Ser Asp Tyr Gln
                665                 670                 675

Gln Ala Pro Gln Leu Ser Pro Val Pro Tyr Val Leu Thr Pro Cys
                680                 685                 690

Asp Gly Leu Leu Val Ser Gly Ile Pro Leu Leu Pro Thr Pro Leu
                695                 700                 705

Leu Gln Pro Gly Met Ser Pro Val Ala Ser Ala Ala Gln Leu Leu
                710                 715                 720

Asp Ala His Leu His Ile Ser Ala Gly Pro Val Ala Leu Pro Thr
                725                 730                 735

Gly Pro Leu Pro Gln Cys Leu Thr Arg Leu Ser Pro Ser Cys Asp
                740                 745                 750

Pro Ala Gly Leu Pro Gln Gly Asp Cys Glu Met Glu Asp Leu Thr
                755                 760                 765

Ser Gly Gln Arg Gly Thr Phe Val Leu Val Gln
                770                 775

<210> SEQ ID NO 35
<211> LENGTH: 604
<212> TYPE: PRT
<213> ORGANISM: Drosophila melanogaster
<220> FEATURE:
```

```
<221> NAME/KEY: misc_feature
<223> OTHER INFORMATION: GenBank Accession No: g2564680
<220> FEATURE:
<221> NAME/KEY: unsure
<222> LOCATION: 52, 291, 354
<223> OTHER INFORMATION: unknown or other

<400> SEQUENCE: 35
```

Met Thr Ala Ala Asn Thr Asn Lys Thr Thr Asp Lys Glu Asn Asp
 1               5                  10                  15

Pro Gly Pro Asn Thr Ser Ile Ser Thr Thr Ala Thr Pro Pro Ser
             20                  25                  30

Ala Ala Ala Gln Asn Val Gly Gly Cys Val Gly Ser Ser Gly Gly
             35                  40                  45

Arg Ser Ser Pro Lys Phe Xaa Ser Tyr Val Asn Gly Asn Gly Tyr
             50                  55                  60

Gly Val Tyr Lys Ile Ile Lys Thr Leu Gly Lys Gly Asn Phe Ala
             65                  70                  75

Lys Val Lys Leu Ala Ile His Leu Pro Thr Gly Arg Glu Val Ala
             80                  85                  90

Ile Lys Leu Ile Asp Lys Thr Ala Leu Asn Thr Ile Ala Arg Gln
             95                 100                 105

Lys Leu Tyr Arg Glu Val Asn Ile Met Lys Lys Leu Asn His Pro
            110                 115                 120

Asn Ile Val Arg Leu Leu Gln Val Ile Glu Ser Glu Arg Thr Leu
            125                 130                 135

Tyr Leu Val Met Glu Tyr Val Ser Gly Gly Glu Leu Phe Asn Tyr
            140                 145                 150

Leu Val Lys Asn Gly Arg Met Arg Glu Arg Asp Ala Arg Val Leu
            155                 160                 165

Phe Arg Gln Leu Val Ser Ala Ile Glu Tyr Cys His Ser Lys Ser
            170                 175                 180

Ile Val His Arg Asp Leu Lys Ala Glu Asn Leu Leu Leu Asp Gln
            185                 190                 195

Gln Met Lys Leu Lys Ile Ala Asp Phe Gly Phe Ser Thr Thr Phe
            200                 205                 210

Glu Pro Lys Ala Pro Leu Glu Thr Phe Cys Gly Ser Pro Pro Tyr
            215                 220                 225

Ala Ala Pro Glu Leu Phe Lys Gly Lys Lys Tyr Ser Gly Pro Glu
            230                 235                 240

Val Asp Ser Trp Ser Leu Gly Val Val Leu Tyr Thr Leu Val Ser
            245                 250                 255

Gly Ser Leu Pro Phe Asp Gly Thr Asn Leu Lys Glu Leu Arg Asp
            260                 265                 270

Arg Val Leu Arg Gly Lys Tyr Arg Val Pro Tyr Tyr Val Ser Ile
            275                 280                 285

Glu Cys Glu Ser Leu Xaa Arg Lys Phe Leu Val Leu Asn Pro Thr
            290                 295                 300

Gln Arg Thr Ser Leu Ser Ala Val Met Ala Asp Arg Trp Ile Asn
            305                 310                 315

Met Gly Tyr Glu Gln Gly Asn Gly Leu Arg Pro Phe Gln Glu Lys
            320                 325                 330

Pro Met Asp Leu His Asp Val Asn Arg Leu Ser Leu Leu Ser Asn
            335                 340                 345

Met Gly His Lys Pro Arg Asp Val Xaa Gln Ser Leu Lys Asn Gln

-continued

```
                    350                 355                 360

Lys Phe Asp Asp Ile Tyr Cys Ala Tyr Met Leu Leu Asp Val Ala
                365                 370                 375

Lys Pro Arg Ser Thr Ala Cys Ser Glu Lys Ser Gly Ser Ser Phe
                380                 385                 390

Arg Glu Thr Pro Thr Ala Met Pro Gly Ser Ser Arg Ile Pro Val
                395                 400                 405

Pro Ile Ala Ala Pro Asn Val Thr Ile Ser Gln Val Thr Phe Ala
                410                 415                 420

Leu Asp Lys Ser Thr Pro Asn Arg Pro Gly Ala Thr Ser Ile Arg
                425                 430                 435

Pro Met Ala Pro Arg Leu Ala Asn Ala Leu Thr Pro Leu Pro Leu
                440                 445                 450

Thr Pro Pro Pro Lys Lys Tyr Ile Cys Cys Ser Ala Ser Lys Ala
                455                 460                 465

Ala Asn Pro Arg Arg Ser Glu Pro Ser Ser Ile Pro Gln Ser Ala
                470                 475                 480

Met Pro Lys Lys Gly Val Gly Ser Pro Val Asp Val Lys Thr Thr
                485                 490                 495

Leu Leu Ser Ala Gln Arg Lys Leu Ala Val Asn His Lys Leu Thr
                500                 505                 510

Ser Ala Ser His Gln Ile Arg Ser Pro Ile Thr Gln Ser Ser Ser
                515                 520                 525

Gln Ala Ser Glu Cys Thr Arg Thr Pro Thr His Phe Glu Met
                530                 535                 540

Leu Asp Ser Thr Ser Thr Pro Leu Lys Val Leu Lys Leu Val Ala
                545                 550                 555

Ser Asn Ser Gln Thr Pro Pro Ser Thr Glu Asn Ile Asn Arg Pro
                560                 565                 570

Thr Arg Val Gly Phe Phe Ser Lys Leu Ser Ala Arg Phe Val Arg
                575                 580                 585

Arg Ser Leu His Lys Gly Glu Lys Asp Ile Ser Glu Gln Gly Arg
                590                 595                 600

Asn Leu Thr Lys

<210> SEQ ID NO 36
<211> LENGTH: 745
<212> TYPE: PRT
<213> ORGANISM: Homo sapiens
<220> FEATURE:
<221> NAME/KEY: misc_feature
<223> OTHER INFORMATION: GenBank Accession No: g1749794

<400> SEQUENCE: 36

Met Ile Arg Gly Arg Asn Ser Ala Thr Ser Ala Asp Glu Gln Pro
  1               5                  10                  15

His Ile Gly Asn Tyr Arg Leu Leu Lys Thr Ile Gly Lys Gly Asn
                 20                  25                  30

Phe Ala Lys Val Lys Leu Ala Arg His Ile Leu Thr Gly Lys Glu
                 35                  40                  45

Val Ala Val Lys Ile Ile Asp Lys Thr Gln Leu Asn Ser Ser Ser
                 50                  55                  60

Leu Gln Lys Leu Phe Arg Glu Val Arg Ile Met Lys Val Leu Asn
                 65                  70                  75

His Pro Asn Ile Val Lys Leu Phe Glu Val Ile Glu Thr Glu Lys
```

-continued

```
                    80                  85                  90
Thr Leu Tyr Leu Val Met Glu Tyr Ala Ser Gly Gly Glu Val Phe
                95                 100                 105
Asp Tyr Leu Val Ala His Gly Arg Met Lys Glu Lys Glu Ala Arg
               110                 115                 120
Ala Lys Phe Arg Gln Ile Val Ser Ala Val Gln Tyr Cys His Gln
               125                 130                 135
Lys Phe Ile Val His Arg Asp Leu Lys Ala Glu Asn Leu Leu Leu
               140                 145                 150
Asp Ala Asp Met Asn Ile Lys Ile Ala Asp Phe Gly Phe Ser Asn
               155                 160                 165
Glu Phe Thr Phe Gly Asn Lys Leu Asp Thr Phe Cys Gly Ser Pro
               170                 175                 180
Pro Tyr Ala Ala Pro Glu Leu Phe Gln Gly Lys Lys Tyr Asp Gly
               185                 190                 195
Pro Glu Val Asp Val Trp Ser Leu Gly Val Ile Leu Tyr Thr Leu
               200                 205                 210
Val Ser Gly Ser Leu Pro Phe Asp Gly Gln Asn Leu Lys Glu Leu
               215                 220                 225
Arg Glu Arg Val Leu Arg Gly Lys Tyr Arg Ile Pro Phe Tyr Met
               230                 235                 240
Ser Thr Asp Cys Glu Asn Leu Leu Lys Lys Phe Leu Ile Leu Asn
               245                 250                 255
Pro Ser Lys Arg Gly Thr Leu Glu Gln Ile Met Lys Asp Arg Trp
               260                 265                 270
Met Asn Val Gly His Glu Asp Asp Glu Leu Lys Pro Tyr Val Glu
               275                 280                 285
Pro Leu Pro Asp Tyr Lys Asp Pro Arg Arg Thr Glu Leu Met Val
               290                 295                 300
Ser Met Gly Tyr Thr Arg Glu Glu Ile Gln Asp Ser Leu Val Gly
               305                 310                 315
Gln Arg Tyr Asn Glu Val Met Ala Thr Tyr Leu Leu Leu Gly Tyr
               320                 325                 330
Lys Ser Ser Glu Leu Glu Gly Asp Thr Ile Thr Leu Lys Pro Arg
               335                 340                 345
Pro Ser Ala Asp Leu Thr Asn Ser Ser Ala Gln Phe Pro Ser His
               350                 355                 360
Lys Val Gln Arg Ser Val Ser Ala Asn Pro Lys Gln Arg Arg Phe
               365                 370                 375
Ser Asp Gln Ala Gly Pro Ala Ile Pro Thr Ser Asn Ser Tyr Ser
               380                 385                 390
Lys Lys Thr Gln Ser Asn Asn Ala Glu Asn Lys Arg Pro Glu Glu
               395                 400                 405
Asp Arg Glu Ser Gly Arg Lys Ala Ser Ser Thr Ala Lys Val Pro
               410                 415                 420
Ala Ser Pro Leu Pro Gly Leu Glu Arg Lys Lys Thr Thr Pro Thr
               425                 430                 435
Pro Ser Thr Asn Ser Val Leu Ser Thr Ser Thr Asn Arg Ser Arg
               440                 445                 450
Asn Ser Pro Leu Leu Glu Arg Ala Ser Leu Gly Gln Ala Ser Ile
               455                 460                 465
Gln Asn Gly Lys Asp Ser Leu Thr Met Pro Gly Ser Arg Ala Ser
               470                 475                 480
```

Thr Ala Ser Ala Ser Ala Ala Val Ser Ala Ala Arg Pro Arg Gln
                485                 490                 495

His Gln Lys Ser Met Ser Ala Ser Val His Pro Asn Lys Ala Ser
                500                 505                 510

Gly Leu Pro Pro Thr Glu Ser Asn Cys Glu Val Pro Arg Pro Ser
                515                 520                 525

Thr Ala Pro Gln Arg Val Pro Val Ala Ser Pro Ser Ala His Asn
                530                 535                 540

Ile Ser Ser Ser Gly Gly Ala Pro Asp Arg Thr Asn Phe Pro Arg
                545                 550                 555

Gly Val Ser Ser Arg Ser Thr Phe His Ala Gly Gln Leu Arg Gln
                560                 565                 570

Val Arg Asp Gln Gln Asn Leu Pro Tyr Gly Val Thr Pro Ala Ser
                575                 580                 585

Pro Ser Gly His Ser Gln Gly Arg Arg Gly Ala Ser Gly Ser Ile
                590                 595                 600

Phe Ser Lys Phe Thr Ser Lys Phe Val Arg Arg Asn Leu Asn Glu
                605                 610                 615

Pro Glu Ser Lys Asp Arg Val Glu Thr Leu Arg Pro His Val Val
                620                 625                 630

Gly Ser Gly Gly Asn Asp Lys Glu Lys Glu Glu Phe Arg Glu Ala
                635                 640                 645

Lys Pro Arg Ser Leu Arg Phe Thr Trp Ser Met Lys Thr Thr Ser
                650                 655                 660

Ser Met Glu Pro Asn Glu Met Met Arg Glu Ile Arg Lys Val Leu
                665                 670                 675

Asp Ala Asn Ser Cys Gln Ser Glu Leu His Glu Lys Tyr Met Leu
                680                 685                 690

Leu Cys Met His Gly Thr Pro Gly His Glu Asp Phe Val Gln Trp
                695                 700                 705

Glu Met Glu Val Cys Lys Leu Pro Arg Leu Ser Leu Asn Gly Val
                710                 715                 720

Arg Phe Lys Arg Ile Ser Gly Thr Ser Met Ala Phe Lys Asn Ile
                725                 730                 735

Ala Ser Lys Ile Ala Asn Glu Leu Lys Leu
                740                 745

<210> SEQ ID NO 37
<211> LENGTH: 28
<212> TYPE: DNA
<213> ORGANISM: Homo sapiens
<220> FEATURE:
<221> NAME/KEY: misc_feature
<223> OTHER INFORMATION: primer:  forward

<400> SEQUENCE: 37
ggttagttac aagcagtcta gtgcaatt                                    28

<210> SEQ ID NO 38
<211> LENGTH: 25
<212> TYPE: DNA
<213> ORGANISM: Homo sapiens
<220> FEATURE:
<221> NAME/KEY: misc_feature
<223> OTHER INFORMATION: primer: reverse

<400> SEQUENCE: 38

-continued

```
tgctaccaga ccctaaagaa agaga                                    25

<210> SEQ ID NO 39
<211> LENGTH: 28
<212> TYPE: DNA
<213> ORGANISM: Homo sapiens
<220> FEATURE:
<221> NAME/KEY: misc_feature
<223> OTHER INFORMATION: Primer: taqman

<400> SEQUENCE: 39
ccctctgtag acacgggacc cttttttg                                 28
```

What is claimed is:

1. A purified nucleic acid molecule or a fragment thereof comprising a polynucleotide encoding the protein having the amino acid sequence of SEQ ID NO:2 or a portion thereof.

2. A composition comprising the nucleic acid molecule of claim 1 or the complement thereof and a reporter molecule.

3. A fragment of the nucleic acid molecule of clam 1 comprising a polynucleotide selected from SEQ ID NOs:1 and 3–23 and the complete complements of SEQ ID NOs:1 and 3–23.

4. A substrate comprising the nucleic acid molecule of claim 1.

5. A probe consisting of the fragment of claim 3.

6. An expression vector comprising the nucleic acid molecule of claim 1.

7. A host cell containing the expression vector of claim 6.

8. A method for producing a protein having the amino acid sequence of SEQ ID NO:2, the method comprising the steps of:

a) culturing the host cell of claim 7 under conditions for the expression of the protein; and b) recovering the protein from the host cell structure.

9. A method for detecting a nucleic acid molecule in a sample, the method comprising the steps of:

a) hybridizing the composition of claim 2 to at least one nucleic acid in the sample, thereby forming a hybridization complex; and b) detecting the hybridization complex, wherein the presence of the hybridization complex indicates the presence of the nucleic acid molecule in the sample.

10. The method of claim 9 further comprising amplifying the nucleic acids of the sample prior to hybridization.

11. A purified nucleic acid molecule comprising the polynucleotide of SEQ ID NO:1.

12. The method of claim 9 wherein the sample is selected from the group consisting of brain, breast, cervix, colon, lung, ovary, and prostate.

* * * * *